United States Patent
Worthington

(10) Patent No.: US 8,563,293 B2
(45) Date of Patent: Oct. 22, 2013

(54) BACTERIOCIN BASED METHODS TO CONTROL LACTIC ACID BACTERIAL GROWTH

(75) Inventor: Ronald E. Worthington, Edwardsville, IL (US)

(73) Assignee: Southern Illinois University Edwardsville, Edwardsville, IL (US)

( * ) Notice: Subject to any disclaimer, the term of this patent is extended or adjusted under 35 U.S.C. 154(b) by 155 days.

(21) Appl. No.: 13/130,546

(22) PCT Filed: Nov. 23, 2009

(86) PCT No.: PCT/US2009/065573
§ 371 (c)(1),
(2), (4) Date: Jul. 12, 2011

(87) PCT Pub. No.: WO2010/060057
PCT Pub. Date: May 27, 2010

(65) Prior Publication Data
US 2011/0262412 A1 Oct. 27, 2011

Related U.S. Application Data

(60) Provisional application No. 61/117,101, filed on Nov. 22, 2008.

(51) Int. Cl.
*C12N 1/20* (2006.01)
(52) U.S. Cl.
USPC ............... 435/252.3; 435/254.2; 435/254.21; 435/254.11; 435/254.22; 435/254.23; 422/1
(58) Field of Classification Search
None
See application file for complete search history.

(56) References Cited

U.S. PATENT DOCUMENTS

| 4,740,593 | A | 4/1988 | Gonzalez et al. |
| 5,722,342 | A | 3/1998 | Line et al. |
| 2006/0154338 | A1 | 7/2006 | Stahl |
| 2006/0216356 | A1 | 9/2006 | Mansfield et al. |
| 2007/0092956 | A1 | 4/2007 | Rajgarhia et al. |

FOREIGN PATENT DOCUMENTS

WO WO2010060054 A1 5/2010

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
International Search Report and Written Opinion for International Publication No. WO2010/060057A1 (PCT/US2009/065573) dated Mar. 17, 2010 (9 pages).
International Search Report and Written Opinion for International Publication No. WO2010/060054A1 (PCT/US2009/065569) dated Mar. 4, 2010 (10 pages).
De Oliva Neto et al., Screening for yeast with antibacterial properties from an ethanol distillery, Bioresource Technology 2004, 92:1-6 (6 pages).

* cited by examiner

*Primary Examiner* — Jennifer Graser
(74) *Attorney, Agent, or Firm* — Polsinelli PC

(57) ABSTRACT

The present invention relates to compositions and methods for protection against bacterial contamination. The invention provides bactericidal yeast expressing bacteriocin proteins and methods of using the bactericidal yeast.

16 Claims, 3 Drawing Sheets

BACTERIOCIN BASED METHODS TO CONTROL LACTIC ACID BACTERIAL GROWTH

CROSS-REFERENCE TO RELATED APPLICATIONS

This application is a national stage application of PCT International Patent Application No. PCT/U.S.2009/065573 filed Nov. 23, 2009 and also claims priority of U.S. Provisional Application Ser. No. 61/117,101 filed on Nov. 22, 2008, the subject matter of each above-mentioned applications are herein being incorporated by reference in their entirety.

FIELD OF INVENTION

The present invention relates to antibacterial proteins and nucleic acid sequences. Specifically, the invention includes antibacterial protein compositions, methods of use, and transgenic organisms encompassing the antibacterial proteins.

BACKGROUND OF INVENTION

Bacteria are everywhere—from our intestinal tract, to soils, rivers, and oceans. For the most part, bacteria are beneficial, acting to degrade organic waste and recycle nutrients back into the food chain. Sometimes, however, bacteria cause problems.

In order to prevent problems associated with bacteria, antibiotics are often added to an environment to suppress bacterial growth. While this treatment can be effective, the USDA has documented the emergence of antibiotic resistant bacterial strains. Since there are limited ways to treat or prevent bacterial contamination, antibiotic resistance would result in frequent problems associated with contamination such as spoilage. There is also a public health risk with the emergence of antibiotic resistance, because often the bacterial species that cause contamination are ubiquitous in the environment and inhabit the intestinal tract of vertebrate animals, including humans. These bacterial strains do cause human infections and such infections would be medically untreatable if they involve antibiotic resistant bacteria.

There is a need to develop methods to limit or eliminate bacterial contamination, are not cost prohibitive, and do not cause harm to the environment or potentially cause antibiotic resistant bacteria. Current methods are costly and may even introduce harmful antibiotic resistant bacteria to our environment. The present invention limits or eliminates bacteria growth and contamination, and provides a solution to the threats of antibiotic resistance emergence at a reasonable cost.

SUMMARY OF THE INVENTION

The present invention relates to any population of cells, whereby at least one cell comprises an antibacterial protein. One object of the present invention is to provide novel bactericidal yeast that reduces or eliminates bacterial contamination. Another object of the invention is to provide bactericidal yeast that expresses a bacteriocin. A further object of the invention is to provide nucleic acid sequences encoding bacteriocin proteins that have been optimized for yeast expression. Specifically, the bactericidal yeast of the invention expresses an antibacterial protein. Preferably, a suitable antibacterial protein is encoded by an amino acid sequence having at least 65, 66, 70, 75, 80, 81, 82, 83, 84, 85, 86, 87, 88, 89, 90, 91, 92, 93, 94, 95, 96, 97, 98, 99%, or more identity to SEQ ID NO: 13, SEQ ID NO: 14, SEQ ID NO: 15, SEQ ID NO: 16, SEQ ID NO: 17, SEQ ID NO: 18, or SEQ ID NO: 19. Also, a suitable antibacterial protein is encoded by a nucleic acid sequence having at least 70, 75, 80, 81, 82, 83, 84, 85, 86, 87, 88, 89, 90, 91, 92, 93, 94, 95, 96, 97, 98, 99%, or more identity to SEQ ID NO: 1, SEQ ID NO: 2, SEQ ID NO: 3, SEQ ID NO: 4, SEQ ID NO: 5, SEQ ID NO: 6, or SEQ ID NO: 7, SEQ ID NO:8, SEQ ID NO 9, SEQ ID NO 10, SEQ ID NO 11 or SEQ ID NO 12.

A suitable population of cells may be prokaryotic or eukaryotic. Exemplary cell types include yeast, fungus, bacteria, insect, plant, or mammalian. Suitable yeast strains include, but are not limited to, *Kluyveromyces lactis, Saccharomyces cerevisiae, Schizosaccharomyces pombe*, and *Candida albicans*. Further, a population of cells may be contained in an organism. Suitable organisms include yeast, plant, fungus, bacteria, and non-human mammalians. Preferably the organism is yeast. A suitable organism of the invention expresses an antibacterial protein. Preferably, the organism expresses at least one antibacterial protein having a nucleic acid sequence having at least 70, 75, 80, 81, 82, 83, 84, 85, 86, 87, 88, 89, 90, 91, 92, 93, 94, 95, 96, 97, 98, 99%, or more identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO 9, SEQ ID NO 10, SEQ ID NO 11 or SEQ ID NO 12. The organism may express at least one antibacterial protein having at least 65, 66, 70, 75, 80, 81, 82, 83, 84, 85, 86, 87, 88, 89, 90, 91, 92, 93, 94, 95, 96, 97, 98, 99%, or more identity to SEQ ID NO: 13, SEQ ID NO: 14, SEQ ID NO: 15, SEQ ID NO: 16, SEQ ID NO: 17, SEQ ID NO: 18, or SEQ ID NO: 19. The organism may express one, two, three, four, five, six, or more antibacterial proteins of the invention. Further, the expression of the antibacterial protein may be environmentally sensitive. A suitable sensitivity may include, but is not limited to, the presence of lactic acid or ethanol.

The invention also provides methods of protecting against bacterial contamination. A method of the invention includes adding bactericidal yeast expressing at least one antibacterial protein of the invention to an environment at risk of bacterial contamination. Another method of the invention includes adding bactericidal yeast expressing at least one antibacterial protein of the invention to a batch solution at risk of bacterial contamination. The batch solution may be in preparation of fermentation, whereby the bactericidal yeast is added as a fermentation ingredient.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
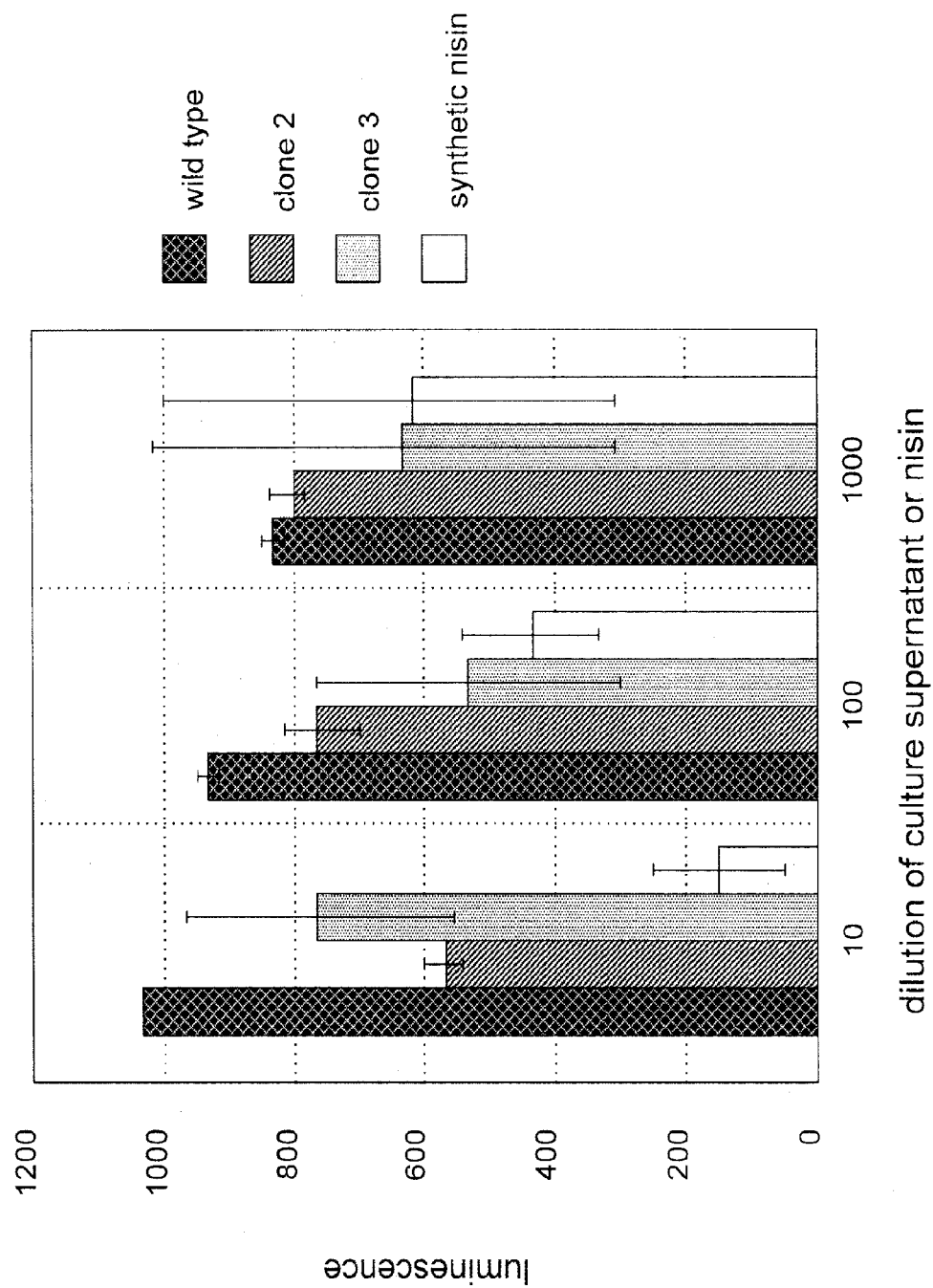
FIG. 1 shows the antibacterial activity of yeast expressing the nisin transgene.

The present invention relates to antibacterial proteins, bactericidal organisms expressing antibacterial proteins, and methods of use. Specifically, proteins having antibacterial activity once secreted from a population of cells or organisms. As such, the methods for use of the antibacterial proteins are also contemplated.

I. Antibacterial Proteins

A. Nucleic Acids Encoding Antibacterial Proteins

Nucleic acids encoding antibacterial proteins (APs) derived from bacterial genomes are disclosed. An AP nucleotide sequence includes an open reading frame that encodes a bacteriocin. In particular, an AP nucleic acid is capable, under appropriate conditions, of expressing a protein having antibacterial activity such as that illustrated by SEQ ID NOs: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO 9, SEQ ID NO 10, SEQ ID NO 11, SEQ ID NO 12, SEQ ID NO: 13, SEQ ID NO: 14, SEQ ID NO: 15, SEQ ID NO: 16, SEQ ID NO: 17, SEQ ID NO: 18, or SEQ ID NO: 19.

AP nucleotides further include nucleic acid sequences that hybridize under high stringency conditions to SEQ ID NOs: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO 9, SEQ ID NO 10, SEQ ID NO 11 or SEQ ID NO 12 such as those that are homologous, substantially similar, or identical to the nucleic acids of the present invention. Homologous nucleic acid sequences will have a sequence similarity of at least about 50%, 55%, 60%, 65%, 70%, 75%, 80%, 85%, 90%, 91%, 92%, 93%, 94%, 95%, 96%, 97%, 98%, 99%, or 100% to any of SEQ ID NOs: SEQ ID NOs: SEQ ID NOs: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO 9, SEQ ID NO 10, SEQ ID NO 11 or SEQ ID NO 12 or the respective complementary sequences. Sequence similarity may be calculated using a number of algorithms known in the art, such as BLAST, described in Altschul, S. F., et al., J. Mol. Biol. 215:403-10, 1990 (using default settings, i.e. parameters w=4 and T=17). The nucleic acids may differ in sequence from the above-described nucleic acids due to the degeneracy of the genetic code. In general, a reference sequence will be 18 nucleotides, more usually 30 or more nucleotides, and may comprise an entire AP sequence for comparison purposes.

Nucleotide sequences that can express an AP, or related protein, and hybridize to the listed nucleotide sequences are contemplated herein. Stringent hybridization conditions include conditions such as hybridization at 50° C. or higher and 0.1×SSC (15 mM sodium chloride/1.5 mM sodium citrate). Another example is overnight incubation at 42° C. in a solution of 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing in 0.1×SSC at about 65° C. Exemplary stringent hybridization conditions are hybridization conditions that are at least about 80%, 85%, 90%, or 95% as stringent as the above specific conditions. Other stringent hybridization conditions are known in the art and may also be employed to identify homologs of the nucleic acids of the invention (Current Protocols in Molecular Biology, Unit 6, pub. John Wiley & Sons, N.Y., 1989).

Mutant nucleotides of the AP proteins may be used, so long as mutants include nucleic acid sequences that encode functional AP proteins as described herein. The subject nucleic acids may be mutated to alter properties of the encoded protein such as expression properties, folding properties, and antibacterial activity. A skilled artisan will recognize that proteins encoded by nucleic acids encoding homologues or mutants may have the same antibacterial properties as the those encoded by SEQ ID NOs: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO 9, SEQ ID NO 10, SEQ ID NO 11 or SEQ ID NO 12 or may have altered antibacterial properties. The DNA sequence or protein product of such a mutation will usually be substantially similar to the sequences provided herein and will differ by one or more nucleotides or amino acids. The sequence changes may be substitutions, insertions, deletions, or a combination thereof. Techniques for mutagenesis of cloned genes are known in the art. Methods for site specific mutagenesis may be found in Gustin et al., Biotechniques 14:22, 1993; Barany, Gene 37:111-23, 1985; Colicelli et al., Mol. Gen. Genet. 199:537-9, 1985; and Sambrook et al., Molecular Cloning: A Laboratory Manual, CSH Press 1989, pp. 15.3-15.108 and all incorporated herein by reference. Such mutated nucleic acid derivatives may be used to study structure-function relationships of a particular AP protein, or to alter properties of the protein that affect its function or regulation. In summary, the invention relates to AP coding sequences such as those of SEQ ID NOs: SEQ ID NOs: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO 9, SEQ ID NO 10, SEQ ID NO 11 or SEQ ID NO 12 and variants or mutants thereof. Also, the invention encompasses the intermediatary RNAs encoded by the described nucleic acid sequences and that translates into an AP of the invention.

In one embodiment nisin, a commercial product used widely in an array of industries, including the food and beverage industry is cloned into the genome of the yeast. Commercial grade nisin has the status of Generally Regarded As Safe (GPAS) under US FDA regulations, and therefore its use could provide immediate impact in many industries after incorporation into the yeast. The unmodified nisin gene can be constructed for incorporation into the yeast according to standards discussed in this specification and known in the industry. By incorporating the nisin into the yeast a nisin yeast strain is created that has antibacterial activity properties.

1. Harmonization of Nucleic Acid Sequences Encoding APs

To circumvent problems associated with poor translation efficiency of non-mammalian derived mRNA in mammalian systems, strategies to harmonize proteins are often used. Harmonizing a protein involves optimizing the nucleotide codons encoding specific amino acids to those more likely to be used in the specific host's genes. For example, GGG, GGA, GGT, and GGC all encode the amino acid Glycine; however, GGT is more often used to encode Glycine in *Kluyeromyces lactis* genes than GGG (Table 1). To increase translation efficiency in yeast cells, at the Glycine position, GGG should be replaced with GGT. Strategies to harmonize proteins are well known in the art and described herein in the Examples.

The present invention provides nucleic acid sequences encoding AP proteins of the invention harmonized for expression in yeast. The nucleic acids SEQ ID NOs: SEQ ID NOs: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO 9, SEQ ID NO 10, SEQ ID NO 11 or SEQ ID NO 12 have been optimized using the preferred codons of yeast genes (Table 1-4) in order to increase protein translation in yeast systems. One skilled in the art will recognize that coding sequences may be optimized for use in any species through codon harmonization.

Preferred codons for protein expression for a wide variety of organisms may be obtained from publicly available codon usage databases. The Codon Usage Database is an extended worldwide web version of CUTG (Codon Usage Tabulated from GenBank) developed and maintained by Yasukazu Nakamura at The First Laboratory for Plant Gene Research, Kazusa DNA Research Institute, Japan. The KEGG (Kyoto Encyclopedia of Genes and Genomes) Database is another database and is described in Aoki and Kanehisa, Current Protocols in Bioinformatics, (2005) 1.12.1-1.12.54, which is incorporated herein by reference.

TABLE 1

Preferred DNA Codons for *Kluyveromyces lactis*.

| Amino Acid | Codon | Number | Frequency/1000 |
|---|---|---|---|
| Gly | GGG | 788.00 | 5.25 |
| Gly | GGA | 1727.00 | 11.50 |
| Gly | GGT | 5335.00 | 35.54 |
| Gly | GGC | 845.00 | 5.63 |
| Glu | GAG | 2393.00 | 15.94 |
| Glu | GAA | 7124.00 | 47.46 |
| Asp | GAT | 6116.00 | 40.74 |
| Asp | GAC | 2762.00 | 18.40 |
| Val | GTG | 1636.00 | 10.90 |
| Val | GTA | 1642.00 | 10.94 |
| Val | GTT | 3893.00 | 25.93 |
| Val | GTC | 2138.00 | 14.24 |
| Ala | GCG | 734.00 | 4.89 |
| Ala | GCA | 2334.00 | 15.55 |
| Ala | GCT | 4217.00 | 28.09 |
| Ala | GCC | 1778.00 | 11.84 |
| Arg | AGG | 902.00 | 6.01 |
| Arg | AGA | 3707.00 | 24.69 |
| Ser | AGT | 1917.00 | 12.77 |
| Ser | AGC | 953.00 | 6.35 |
| Lys | AAG | 5070.00 | 33.77 |
| Lys | AAA | 5629.00 | 37.50 |
| Asn | AAT | 4735.00 | 31.54 |
| Asn | AAC | 3829.00 | 25.51 |
| Met | ATG | 3158.00 | 21.04 |
| Met | ATA | 2368.00 | 15.77 |
| Ile | ATT | 4123.00 | 27.46 |
| Ile | ATC | 3138.00 | 20.90 |
| Thr | ACG | 874.00 | 5.82 |
| Thr | ACA | 2282.00 | 15.20 |
| Thr | ACT | 3444.00 | 22.94 |
| Thr | ACC | 1923.00 | 12.81 |
| Trp | TGG | 1697.00 | 11.30 |
| Trp | TGA | 83.00 | 0.55 |
| Cys | TGT | 1433.00 | 9.55 |
| Cys | TGC | 483.00 | 3.22 |
| End | TAG | 55.00 | 0.37 |
| End | TAA | 163.00 | 1.09 |
| Tyr | TAT | 3033.00 | 20.20 |
| Tyr | TAC | 2557.00 | 17.03 |
| Leu | TTG | 5083.00 | 33.86 |
| Leu | TTA | 3534.00 | 23.54 |
| Phe | TTT | 2929.00 | 19.51 |
| Phe | TTC | 3534.00 | 23.54 |
| Ser | TCG | 1150.00 | 7.66 |
| Ser | TCA | 2445.00 | 16.29 |
| Ser | TCT | 4012.00 | 26.73 |
| Ser | TCC | 1901.00 | 12.66 |
| Arg | CGG | 224.00 | 1.49 |
| Arg | CGA | 318.00 | 2.12 |
| Arg | CGT | 1001.00 | 6.67 |
| Arg | CGC | 228.00 | 1.52 |
| Gln | CAG | 1769.00 | 11.78 |
| Gln | CAA | 4411.00 | 29.38 |
| His | CAT | 2130.00 | 14.19 |
| His | CAC | 1043.00 | 6.95 |
| Thr | CTG | 770.00 | 5.13 |
| Thr | CTA | 1766.00 | 11.76 |
| Thr | CTT | 1779.00 | 11.85 |
| Thr | CTC | 649.00 | 4.32 |
| Pro | CCG | 633.00 | 4.22 |
| Pro | CCA | 3201.00 | 21.32 |
| Pro | CCT | 2020.00 | 13.46 |
| Pro | CCC | 573.00 | 3.82 |

TABLE 2

Preferred DNA Codons for *Saccharomyces cerevisiae*.

| Amino Acid | Codon | Number | Frequency/1000 |
|---|---|---|---|
| Gly | GGG | 39359.00 | 6.02 |
| Gly | GGA | 71216.00 | 10.90 |
| Gly | GGT | 156109.00 | 23.89 |
| Gly | GGC | 63903.00 | 9.78 |
| Glu | GAG | 125717.00 | 19.24 |
| Glu | GAA | 297944.00 | 45.60 |
| Asp | GAT | 245641.00 | 37.59 |
| Asp | GAC | 132048.00 | 20.21 |
| Val | GTG | 70337.00 | 10.76 |
| Val | GTA | 76927.00 | 11.77 |
| Val | GTT | 144243.00 | 22.07 |
| Val | GTC | 76947.00 | 11.78 |
| Ala | GCG | 40358.00 | 6.18 |
| Ala | GCA | 105910.00 | 16.21 |
| Ala | GCT | 138358.00 | 21.17 |
| Ala | GCC | 82357.00 | 12.60 |
| Arg | AGG | 60289.00 | 9.23 |
| Arg | AGA | 139081.00 | 21.28 |
| Ser | AGT | 92466.00 | 14.15 |
| Ser | AGC | 63726.00 | 9.75 |
| Lys | AAG | 201361.00 | 30.82 |
| Lys | AAA | 273618.00 | 41.87 |
| Asn | AAT | 233124.00 | 35.68 |
| Asn | AAC | 162199.00 | 24.82 |
| Met | ATG | 136805.00 | 20.94 |
| Met | ATA | 116254.00 | 17.79 |
| Ile | ATT | 196893.00 | 30.13 |
| Ile | ATC | 112176.00 | 17.17 |
| Thr | ACG | 52045.00 | 7.96 |
| Thr | ACA | 116084.00 | 17.76 |
| Thr | ACT | 132522.00 | 20.28 |
| Thr | ACC | 83207.00 | 12.73 |
| Trp | TGG | 67789.00 | 10.37 |
| Trp | TGA | 4447.00 | 0.68 |
| Cys | TGT | 52903.00 | 8.10 |
| Cys | TGC | 31095.00 | 4.76 |
| End | TAG | 3312.00 | 0.51 |
| End | TAA | 6913.00 | 1.06 |
| Tyr | TAT | 122728.00 | 18.78 |
| Tyr | TAC | 96596.00 | 14.78 |
| Leu | TTG | 177573.00 | 27.17 |
| Leu | TTA | 170884.00 | 26.15 |
| Phe | TTT | 170666.00 | 26.12 |
| Phe | TTC | 120510.00 | 18.44 |
| Ser | TCG | 55951.00 | 8.56 |
| Ser | TCA | 122028.00 | 18.67 |
| Ser | TCT | 153557.00 | 23.50 |
| Ser | TCC | 92923.00 | 14.22 |
| Arg | CGG | 11351.00 | 1.74 |
| Arg | CGA | 19562.00 | 2.99 |
| Arg | CGT | 41791.00 | 6.40 |
| Arg | CGC | 16993.00 | 2.60 |
| Gln | CAG | 79121.00 | 12.11 |
| Gln | CAA | 178251.00 | 27.28 |
| His | CAT | 89007.00 | 13.62 |
| His | CAC | 50785.00 | 7.77 |
| Thr | CTG | 68494.00 | 10.48 |
| Thr | CTA | 87619.00 | 13.41 |
| Thr | CTT | 80076.00 | 12.25 |
| Thr | CTC | 35545.00 | 5.44 |
| Pro | CCG | 34597.00 | 5.29 |
| Pro | CCA | 119641.00 | 18.31 |
| Pro | CCT | 88263.00 | 13.51 |
| Pro | CCC | 44309.00 | 6.78 |

TABLE 3

Preferred DNA Codons for *Schizosaccharomyces pombe*.

| Amino Acid | Codon | Number | Frequency |
|---|---|---|---|
| Gly | GGG | 12611.00 | 4.41 |
| Gly | GGA | 45350.00 | 15.86 |

TABLE 3-continued

Preferred DNA Codons for *Schizosaccharomyces pombe*.

| Amino Acid | Codon | Number | Frequency |
|---|---|---|---|
| Gly | GGT | 61455.00 | 21.49 |
| Gly | GGC | 23819.00 | 8.33 |
| Glu | GAG | 60189.00 | 21.05 |
| Glu | GAA | 126924.00 | 44.39 |
| Asp | GAT | 108632.00 | 37.99 |
| Asp | GAC | 44870.00 | 15.69 |
| Val | GTG | 23799.00 | 8.32 |
| Val | GTA | 35383.00 | 12.37 |
| Val | GTT | 82961.00 | 29.01 |
| Val | GTC | 30476.00 | 10.66 |
| Ala | GCG | 15402.00 | 5.39 |
| Ala | GCA | 45581.00 | 15.94 |
| Ala | GCT | 85195.00 | 29.79 |
| Ala | GCC | 32882.00 | 11.50 |
| Arg | AGG | 14555.00 | 5.09 |
| Arg | AGA | 32175.00 | 11.25 |
| Ser | AGT | 42557.00 | 14.88 |
| Ser | AGC | 26242.00 | 9.18 |
| Lys | AAG | 70110.00 | 24.52 |
| Lys | AAA | 113860.00 | 39.82 |
| Asn | AAT | 97492.00 | 34.10 |
| Asn | AAC | 51016.00 | 17.84 |
| Met | ATG | 59444.00 | 20.79 |
| Met | ATA | 38588.00 | 13.50 |
| Ile | ATT | 100275.00 | 35.07 |
| Ile | ATC | 36129.00 | 12.64 |
| Thr | ACG | 18756.00 | 6.56 |
| Thr | ACA | 40864.00 | 14.29 |
| Thr | ACT | 65826.00 | 23.02 |
| Thr | ACC | 30616.00 | 10.71 |
| Trp | TGG | 31666.00 | 11.07 |
| Trp | TGA | 1228.00 | 0.43 |
| Cys | TGT | 25792.00 | 9.02 |
| Cys | TGC | 15958.00 | 5.58 |
| End | TAG | 1282.00 | 0.45 |
| End | TAA | 3622.00 | 1.27 |
| Tyr | TAT | 63277.00 | 22.13 |
| Tyr | TAC | 33662.00 | 11.77 |
| Leu | TTG | 68803.00 | 24.06 |
| Leu | TTA | 75328.00 | 26.34 |
| Phe | TTT | 92872.00 | 32.48 |
| Phe | TTC | 37197.00 | 13.01 |
| Ser | TCG | 23155.00 | 8.10 |
| Ser | TCA | 51773.00 | 18.11 |
| Ser | TCT | 86624.00 | 30.29 |
| Ser | TCC | 34753.00 | 12.15 |
| Arg | CGG | 8560.00 | 2.99 |
| Arg | CGA | 22918.00 | 8.01 |
| Arg | CGT | 44685.00 | 15.63 |
| Arg | CGC | 17213.00 | 6.02 |
| Gln | CAG | 31063.00 | 10.86 |
| Gln | CAA | 78435.00 | 27.43 |
| His | CAT | 46721.00 | 16.34 |
| His | CAC | 18013.00 | 6.30 |
| Thr | CTG | 18453.00 | 6.45 |
| Thr | CTA | 24965.00 | 8.73 |
| Thr | CTT | 72340.00 | 25.30 |
| Thr | CTC | 20752.00 | 7.26 |
| Pro | CCG | 13034.00 | 4.56 |
| Pro | CCA | 36383.00 | 12.72 |
| Pro | CCT | 61687.00 | 21.57 |
| Pro | CCC | 23151.00 | 8.10 |

TABLE 4

Preferred DNA Codons for *Candida albicans*.

| Amino Acid | Codon | Number | Frequency/1000 |
|---|---|---|---|
| Gly | GGG | 4945.00 | 7.78 |
| Gly | GGA | 8710.00 | 13.70 |
| Gly | GGT | 18556.00 | 29.19 |
| Gly | GGC | 2818.00 | 4.43 |
| Glu | GAG | 7547.00 | 11.87 |
| Glu | GAA | 31701.00 | 49.87 |
| Asp | GAT | 27797.00 | 43.73 |
| Asp | GAC | 8545.00 | 13.44 |
| Val | GTG | 6612.00 | 10.40 |
| Val | GTA | 5460.00 | 8.59 |
| Val | GTT | 19155.00 | 30.14 |
| Val | GTC | 5773.00 | 9.08 |
| Ala | GCG | 1346.00 | 2.12 |
| Ala | GCA | 10162.00 | 15.99 |
| Ala | GCT | 17393.00 | 27.36 |
| Ala | GCC | 7453.00 | 11.73 |
| Arg | AGG | 1834.00 | 2.89 |
| Arg | AGA | 13817.00 | 21.74 |
| Ser | AGT | 11094.00 | 17.45 |
| Ser | AGC | 2955.00 | 4.65 |
| Lys | AAG | 11660.00 | 18.34 |
| Lys | AAA | 31114.00 | 48.95 |
| Asn | AAT | 27162.00 | 42.73 |
| Asn | AAC | 11560.00 | 18.19 |
| Met | ATG | 11591.00 | 18.24 |
| Met | ATA | 9127.00 | 14.36 |
| Ile | ATT | 25761.00 | 40.53 |
| Ile | ATC | 8590.00 | 13.51 |
| Thr | ACG | 2501.00 | 3.93 |
| Thr | ACA | 11928.00 | 18.77 |
| Thr | ACT | 19438.00 | 30.58 |
| Thr | ACC | 8567.00 | 13.48 |
| Trp | TGG | 6942.00 | 10.92 |
| Trp | TGA | 180.00 | 0.28 |
| Cys | TGT | 5964.00 | 9.38 |
| Cys | TGC | 1135.00 | 1.79 |
| End | TAG | 336.00 | 0.53 |
| End | TAA | 632.00 | 0.99 |
| Tyr | TAT | 16146.00 | 25.40 |
| Tyr | TAC | 6614.00 | 10.41 |
| Leu | TTG | 21993.00 | 34.60 |
| Leu | TTA | 22928.00 | 36.07 |
| Phe | TTT | 18958.00 | 29.83 |
| Phe | TTC | 9899.00 | 15.57 |
| Ser | TCG | 4341.00 | 6.83 |
| Ser | TCA | 16751.00 | 26.35 |
| Ser | TCT | 13984.00 | 22.00 |
| Ser | TCC | 6145.00 | 9.67 |
| Arg | CGG | 604.00 | 0.95 |
| Arg | CGA | 2604.00 | 4.10 |
| Arg | CGT | 3791.00 | 5.96 |
| Arg | CGC | 523.00 | 0.82 |
| Gln | CAG | 4163.00 | 6.55 |
| Gln | CAA | 22696.00 | 35.71 |
| His | CAT | 9373.00 | 14.75 |
| His | CAC | 3578.00 | 5.63 |
| Thr | CTG | 2201.00 | 3.46 |
| Thr | CTA | 2782.00 | 4.38 |
| Thr | CTT | 6456.00 | 10.16 |
| Thr | CTC | 1636.00 | 2.57 |
| Pro | CCG | 1721.00 | 2.71 |
| Pro | CCA | 16709.00 | 26.29 |
| Pro | CCT | 8495.00 | 13.36 |
| Pro | CCC | 2665.00 | 4.19 |

B. Protein/Polypeptide Compositions

The invention contemplates antibacterial proteins (APs) and mutants thereof, which include those proteins encoded by the subject nucleic acids, as well as polypeptides comprising the antibacterial proteins. The isolated antibacterial proteins of the invention are exemplified by the sequences of SEQ ID NOs: SEQ ID NO: 13, SEQ ID NO: 14, SEQ ID NO: 15, SEQ ID NO: 16, SEQ ID NO: 17, SEQ ID NO: 18, or SEQ ID NO: 19. Further, the invention includes both the full-length proteins, as well as portions or fragments thereof, and optionally peptides. Additionally, the invention includes variations of the naturally occurring proteins, where such variations are homologous or substantially similar to the naturally occurring proteins, and mutants of the naturally occurring proteins, as described herein.

Homologs or proteins (or fragments thereof) that vary in sequence from the amino acid sequences SEQ ID NOs: SEQ ID NO: 13, SEQ ID NO: 14, SEQ ID NO: 15, SEQ ID NO: 16, SEQ ID NO: 17, SEQ ID NO: 18, or SEQ ID NO: 19 are also included in the invention. By homolog is meant a protein having at least about 10%, usually at least about 25%, 30%, 40%, 45%, 50%, 55%, 60%, 65%, 70%, 75%, 80%, 85%, 90%, 95%, 99% or higher amino acid sequence identity to the proteins encoded by SEQ ID NOs: 8-12, as determined using MegAlign, DNAstar (1998) clustal algorithm as described in Higgins, D. G. and Sharp, P. M., Fast and Sensitive Multiple Sequence Alignments on a Microcomputer, CABIOS, 5: 151-153, 1989, both incorporated herein by reference.

APs of the invention may be mutated, or altered, to enhance, or change, biological properties of the protein. Such biological properties include, but are not limited to, in vivo or in vitro stability (e.g., half-life) and antibacterial activity. Suitable mutations include single amino acid changes, deletions of one or more amino acids, N-terminal truncations, C-terminal truncations, insertions, etc. Mutants can be generated using standard techniques of molecular biology, including random mutagenesis and targeted mutagenesis as described in Current Protocols in Molecular Biology, Unit 8, pub, John Wiley & Sons, Inc., 2000 and incorporated herein by reference.

Suitable mutants include an amino acid sequence encoded by an open reading frame (ORF) of the gene encoding the subject isolated protein, including the full length protein and fragments thereof, particularly biologically active fragments and fragments corresponding to functional domains, and the like; and including fusions of the subject polypeptides to other proteins or parts thereof. Fragments of interest will typically be at least about 10 amino acids (aa) in length, usually at least about 30, 40, or 50 aa in length, more preferably about 60, 70, 80, 90, 100, 110, 120, 130, 140, or 150 aa in length and may be as long as about 160, 170, 180, 190, 200, 220, 240, 260, 280 or 300 aa in length or even longer, but will usually not exceed about 450 aa in length, where the fragment will have a stretch of amino acids that is identical to the subject protein of at least about 10 aa, and usually at least about 15 aa, and in many embodiments at least about 50, 60, 70, 80, 90, 100, 110, 120, 130, 140, or 150 aa in length. The subject polypeptides can be about 25 aa, about 50 aa, about 75 aa, about 100 aa, about 125 aa, about 150 aa, about 200 aa, about 210 aa, about 220 aa, about 230 aa, or about 240 aa in length, up to and including the entire protein. A skilled artisan will recognize that a protein fragment may retain all or substantially all of a biological property of the protein.

1. AP Characteristics

The proteins and polypeptides of the invention are characterized by having antibacterial activity. Specifically, the proteins of the invention are bacteriocins having antibacterial activity. Bacteriocins are proteins made by bacteria that are capable of forming pores in other bacteria, leading to the bacteria's destruction. Bacteria generate bacteriocins to compete with other bacteria in an environment for nutrients.

The APs of the invention may further include additional components that enhance their expression. Such additional components include promoters, enhancers, secretion signals, etc. For example, the AP sequence may include a host specific secretion signal. An exemplary secretion signal would include, but is not limited to, a yeast signal peptide sequence that mediates secretion of the AP gene product. Further, the AP sequence may include, or be under the control of, an inducible or constitutive promoter. Such promoters may be environmentally sensitive to specific substances. By way of example, a promoter may be sensitive to lactic acid, such as the LDH promoter. In the presence of lactic acid, the promoter activates transcription of the downstream gene. Likewise, a promoter may be activated by a transcription factor that is sensitive to a substance, such as the alcohol dehydrogenase I promoter of Aspergillus nidulans. In the presense of ethanol, the alcR transcription factor binds to the alcA binding domain in the alcohol dehydrogenase I promoter and activates transcription of the downstream gene. Methods for using inducible promoters are described in the art as well as in the Examples herein.

The subject proteins typically range in length from about 50 to 200 residues and included herein are specific examples that are about 40, 46, 47, 49, 71, and 73 amino acid residues in length. The subject proteins include both shorter and longer variants that range in length from as short as about 15, 20, 25, 30, 35, 40, 50, or 60 or even longer. The subject proteins generally have a molecular weight ranging from about 3 to 15 kDa, including specifically about 4.6, 5.0, 5.4, 7.5, and 7.7 kDa.

2. AP Production

The present invention includes a method of producing an AP by cultivating a host cell expressing an AP and then isolating the protein. Such methods include the introduction of an expression vector containing at least one protein coding sequence of the invention into a host cell, as described herein, cultivation of the subject protein containing host cell, and isolation of the subject protein from the cell extract. The expressed subject protein may or may not be linked to another protein of interest. Methods to cultivate host cells are known in the art. Methods to express and isolate a subject protein are described in Current Protocols in Protein Science, Units 5, pub. John Wiley & Sons, Inc., 2002 and Current Protocols in Protein Science, Units 6, pub. John Wiley & Sons, Inc., 2002 and both are incorporated herein by reference.

C. Expression System for APs

1. Vectors

Methods for introducing a DNA sequence into eukaryotic cells are known in the art and typically include the use of a DNA vector or plasmid. There are many vectors known and available in the art that are useful for the polynucleotides of the invention. One of skill in the art will recognize that the selection of a particular vector depends upon the intended use of the polynucleotide. Preferably, the DNA sequences are introduced by a vector, or plasmid, capable of transforming and driving the expression of the components of the construct in the desired cell type, whether that cell type is prokaryotic or eukaryotic. Many vectors comprise sequences allowing both prokaryotic vector replication and eukaryotic expression of operably linked gene sequences.

Figure 2:
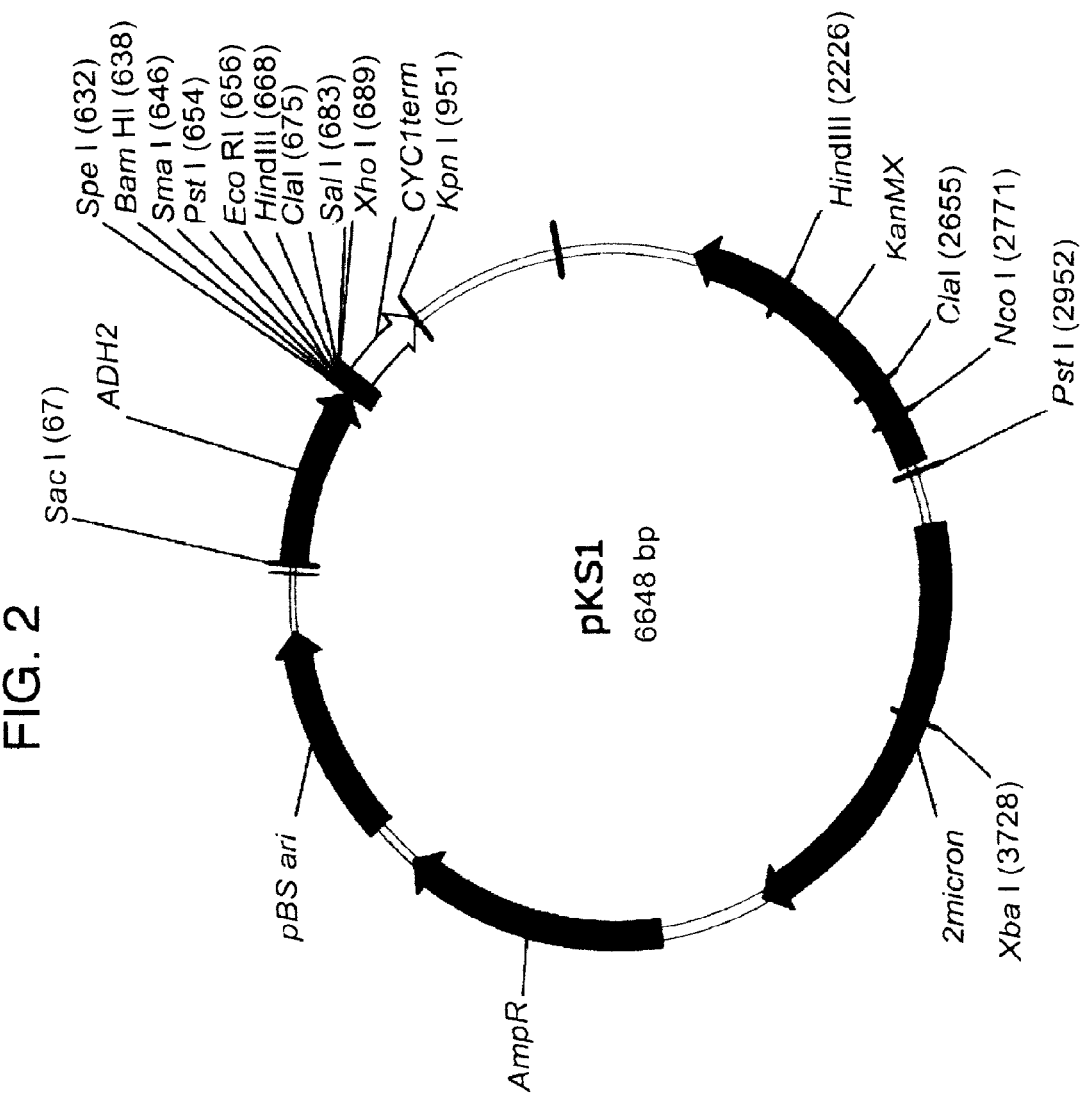
FIG. 2 demonstrates the pKS1 vector used to create pKS1-suc.

In one embodiment a suitable shuttle vector was created based on the plasmid pKS1 from Dual Biosystems (Basel, Switzerland). The pKS1 plasmid was re-engineered (pKS1-suc2) according to industry standards the resulting plasmid is encoded by the nucleic acid sequence having at least 70, 75, 80, 81, 82, 83, 84, 85, 86, 87, 88, 89, 90, 91, 92, 93, 94, 95, 96, 97, 98, 99%, or more identity to SEQ ID NO: 20 or 21. The pKS1-suc2 included the fusion of a S. cervisiae invertase enzyme secretory leader peptide sequence suc2 to the eight amino acid strep II sequence (FIG. 2). Further, the bacteriocin peptides and lysine enzymes were resynthesized with BamHI 5-prime and SalI or XhoI 3-prime termini for in frame cloning with the suc2 secretory peptide and cleavage site. SEQ ID NO 20 or 21.

Vectors useful according to the invention may be autonomously replicating, that is, the vector exists extrachromosomally, and its replication is not necessarily directly linked to the replication of the host genome. Alternatively, the replication of the vector may be linked to the replication of the host chromosomal DNA. For example, the vector may be integrated into a chromosome of the host cell as achieved by retroviral vectors.

A vector will comprise sequences operably linked to the coding sequence of the subject polypeptide that permit the transcription and translation of the components when appropriate. Within the expression vector, a subject polynucleotide is linked to a regulatory sequence as appropriate to obtain the desired expression properties. These regulatory sequences may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as environment specific promoters. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

In one embodiment the pKS1-suc2 plasmid was designed to include regulatory sequences such as promoters. The promoters are designed to ensure expression such that is in an "on" state. The use of promoters are encoded by the nucleic acid sequences having at least 70, 75, 80, 81, 82, 83, 84, 85, 86, 87, 88, 89, 90, 91, 92, 93, 94, 95, 96, 97, 98, 99%, or more identity to SEQ ID NOs: 22-27. These include the promoter regions that are the most highly expressed genes of S. cerevisiae. In one embodiment these include, but are not limited to PMA1 Plasma membrane H+-ATPase; TDH2 Glyceraldehyde-3-phosphate dehydrogenase, isozyme 2; ILV5 Acetohydroxyacid reductoisomerase; FBA1 Fructose 1,6-bisphosphate aldolase; DLD1 D-lactate dehydrogenase; CWP2 Covalently linked cell wall mannoprotein. These regions comprise approximately 1200 base pairs immediately 5-prime of the transcription start site for the given genes. The sequences were determined by promoter analysis using the UCSC Genome Browser. The promoter sequences have SacI 5-prime and SpeI 3-prime sites to allow substitution of the ADH2 promoter of pKS1.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as is known in the art.

A skilled artisan will recognize that the choice of vector for use with the invention is dependent on the host with which the invention will be utilized. Suitable vectors include, but are not limited to, bacteriophage-derived vectors, viral vectors, retroviral vectors, adenoviral vectors, adeno-associated viral vectors, herpesviral vectors, and insect vector systems. Such vectors are well known in the art.

2. Expression Cassettes

Expression cassettes may include a transcription initiation region, at least one polynucleotide of the invention, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the polynucleotides of the invention. After introduction of the DNA, the cells containing the construct may be selected by means of a selectable marker, the cells expanded and then used for expression.

3. Constructs

The term "construct" as used herein refers to a nucleic acid sequence containing at least one AP polynucleotide of the invention operably linked or fused to additional nucleic acids. Such constructs include vectors, plasmids, and expression cassettes encoding at least one polynucleotide of the invention. Constructs may be polynucleotides of the invention fused to other protein coding sequence to generate fusion proteins as described herein. For example, a polynucleotide may be operably linked or fused to a nucleotide sequence encoding a luciferase, luciferin, fluorescence tag, or other identifiable label known in the art.

4. Host Cells

Any cell into which a construct of the invention may be introduced and expressed is useful according to the invention. That is, because of the wide variety of uses for the constructs of the invention, any cell in which a construct of the invention may be expressed, and preferably detected, is a suitable host. The construct may exist in a host cell as an extrachromosomal element or be integrated into the host genome.

Host cells may be prokaryotic, such as any of a number of bacterial strains, or may be eukaryotic, such as yeast or other fungal cells, insect, plant, amphibian, or mammalian cells including, for example, rodent, simian or human cells. Host cells may be primary cultured cells, for example primary human fibroblasts or keratinocytes, or may be an established cell line, such as NIH3T3, 293T or CHO cells among others. Further, mammalian cells useful for expression of the constructs may be phenotypically normal or oncogenically transformed. It is assumed that one skilled in the art can readily establish and maintain a chosen host cell type in culture.

For large scale production of the protein, a unicellular organism, such as E. coli, B. subtilis, S. cerevisiae, insect cells in combination with baculovirus vectors, or cells of a higher organism such as vertebrates, e.g. COS 7 cells, HEK 293, CHO, Xenopus Oocytes, etc., may be used as the expression host cells. In some situations, it is desirable to express the construct in eukaryotic cells, where the expressed protein will benefit from native folding and post-translational modifications. Small peptides may also be synthesized in the laboratory. Polypeptides that are subsets of the complete protein sequence may be used to identify and investigate parts of the protein important for function. Specific expression systems of interest include bacterial, yeast, insect cell, and mammalian cell derived expression systems such as those described in U.S. Pat. No. 6,969,597 and incorporated herein by reference.

In a preferred embodiment, the proteins of the invention are expressed in yeast. Suitable yeast species include those known in the art. Exemplary yeast species include, but are not limited to, *Saccharomyces* species, *Cryptococcus* species, *Kluyveromyces* species, *Sporobolomyces* species, *Rhodotorula* species, *Brettanomyces* species, *Zygosaccharomyces* species, *Aureobasidium* species, and others known in the art. Exemplary species types include *Saccharomyces cerevisiae, Kluyveromyces lactis, Schizosaccharomyces pombe, Candida albicans, Saccharomyces pastorianus, Saccharomyces exiguous, Yarrowia lipolytica*, genetically engineered yeast including those engineered to ferment xylose, *Brettanomyces bruxellensis, Candida stellata, Torulaspora delbrueckii, Zygosaccharomyces bailii, Saccharomyces boulardii,*

*Rhodotorula rubra, Rhodotorula glutinis, Rhodotorula marina, Rhodotorula aurantiaca, Cryptococcus albidus, Cryptococcus diffluens, Cryptococcus laurentii, Saccharomyces rosei, Saccharomyces pretoriensis, Saccharomyces cerevisiae, Sporobolomyces rosues, Sporobolomyces odorus, Kluyveromyces veronae, Aureobasidium pollulans* and others known in the art. A skilled artisan will recognize that the choice of yeast species depends upon the intended use since each yeast species has different physiological and fermentative properties.

When any of the above host cells, or other appropriate host cells or organisms, are used to replicate or express the polynucleotides or nucleic acids of the invention, the resulting replicated nucleic acid, RNA, expressed protein or polypeptide, is within the scope of the invention as a product of the host cell or organism. The product may be recovered by any appropriate means known in the art.

5. Introduction of Constructs to Host Cells

Constructs provided by the invention, including vectors, plasmids, and expression cassettes containing polynucleotides of the invention, may be introduced to selected host cells by any of a number of suitable methods known to those skilled in the art. Constructs may be inserted into mammalian host cells by methods including, but not limited to, electroporation, transfection, microinjection, micro-vessel transfer, particle bombardment, biolistic particle delivery, liposome mediated transfer and other methods described in Current Protocols in Cell Biology, Unit 20, pub. John Wiley & Sons, Inc., 2004 and incorporated herein by reference.

For example, for the introduction of a construct containing vectors into yeast or other fungal cells, chemical transformation methods are generally used (as described by Rose et al., 1990, Methods in Yeast Genetics, Cold Spring Harbor Laboratory Press, Cold Spring Harbor, N.Y. and incorporated herein by reference). For transformation of S. cerevisiae, for example, the cells are treated with lithium acetate. Transformed cells are then isolated on selective media appropriate to the selectable marker used. Other methods known in the art may be used as well as those described in the Examples herein.

Constructs may be introduced to appropriate bacterial cells by infection, as in the case of *E. coli* bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, Molecular Cloning, A Laboratory Manual, Cold Spring Harbor Laboratory Press, Cold Spring Harbor, N.Y., incorporated herein by reference), electroporation may also be used (Current Protocols in Molecular Biology, pub. John Wiley & Sons, Inc., 1993 and incorporated herein by reference).

For the introduction into insect cells, liposome-mediated transfection is commonly used, as is baculovirus infection. Cells such as Schneider-2 cells (*Drosophila melanogaster*), Sf-9 and Sf-21 cells (Spodoptera frugiperda) or High Five™ cells (*Trichoplusia ni*) may be transfected using any of a number of commercially available liposome transfection reagents optimized for use with insect cells. Additionally, particle bombardment, biolistic particle delivery, and micro-injection are widely used to transform insects.

II. Methods of Use

A skilled artisan will recognize that the AP proteins of the invention have many potential uses. Specifically, the expression of the AP proteins by host cells is useful in situations in which the environment of the host cell has the potential of becoming contaminated by bacteria. By way of example, the AP proteins may be particularly useful in the science, food, energy, and pharmaceutical industries. By further example, the AP proteins may be used for, but not limited to, the following products: wine production, beer production, spirit production (i.e. whiskey), beverages, carbonated beverages, food, probiotic supplements, nutritional supplements, nutritional yeast products, bioremediation, ethanol production, as biosensors, screening assays, human or animal pharmaceuticals, medical purposes, such as prevention of tooth decay and other uses.

A method of the invention includes providing a bactericidal organism to an environment at risk of bacterial contamination. Suitable environments include those in which the organism is viable. A skilled artisan will recognize that the environment may be limited by the nutrients required by the bactericidal organism. Preferably, the bactericidal organism is yeast.

Another method of the invention includes providing a bactericidal organism to a batch solution. Suitable batch solutions include those in which the organism is viable. Exemplary batch solutions include, but are not limited to, solutions prepared for fermentation processing and solutions at risk of contamination. A skilled artisan will recognize that the environment may be limited by the nutrients required by the bactericidal organism. Preferably, the bactericidal organism is yeast.

DEFINITIONS

As used herein, the term "bactericidal" refers to the expression of an antibacterial protein. The term is used herein to describe populations of cells and organisms that express at least one antibacterial protein of the invention.

The term "harmonization" or "harmonizing" or their variants refer to altering the nucleotide codons encoding specific amino acids to those more likely to be used in the host cell or organism without altering the encoded amino acid.

An "amino acid (aminocarboxylic acid)" is a component of proteins and peptides. All amino acids contain a central carbon atom to which an amino group, a carboxyl group, and a hydrogen atom are attached. Joining together amino acids forms polypeptides. "Polypeptides" are molecules containing up to 1000 amino acids. "Proteins" are polypeptide polymers containing 50 or more amino acids.

A "gene" is a hereditary unit that has one or more specific effects upon the phenotype of the organism; and the gene can mutate to various allelic forms. The gene is generally comprised of DNA.

The term "variant" relates to nucleotide or amino acid sequences which have similar sequences and that function in the same way.

A "host" is a cell or organism that receives a foreign biological molecule, including a genetic construct or antibody, such as a vector containing a gene.

A "nucleotide sequence" or "nucleic acid molecule" is a nucleotide polymer including genes, gene fragments, oligonucleotides, polynucleotides, and other nucleic acid sequences. "Nucleic acid" refers to the monomeric units from which DNA or RNA polymers are constructed, wherein the unit consists of a purine or pyrimidine base, a pentose, and a phosphoric acid group.

"Plasmids" are double-stranded, closed DNA molecules. Plasmids or "expression vectors" can contain coding sequences for expression machinery such as promoters, poly-A tails, stop codons, and other components necessary for expression of an inserted gene. Plasmids are used as vectors for transfecting a host with a nucleic acid molecule.

A "vector" is a replicon, such as plasmid, phage or cosmid, to which another DNA segment may be attached so as to bring about the replication of the attached segment.

A "population of cells" includes any cell or group of cells. A population of cells may include one or more stem cells and/or one or more progeny cells of a stem cell. Such population of cells can comprise a cell in culture, comprise in vitro tissue, or comprise a tissue within a living organism. The population of cells may be mammalian and includes, but is not limited to, yeast, murine, human, bovine, porcine, equine, ovine, or canine.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of being bound by RNA polymerase, whereby the polymerase initiates transcription of a downstream (3' direction) coding sequence. For purposes of defining the present invention, the promoter sequence includes the minimum number of bases or elements necessary to initiate transcription at levels detectable above background. Within the promoter sequence will be found a transcription initiation site, as well as protein binding domains responsible for the binding of RNA polymerase. Various promoters, including inducible promoters, may be used to drive the various vectors of the present invention.

As used herein, the terms "restriction endonucleases" and "restriction enzymes" refer to enzymes that cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue).

The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a nucleic acid, a protein, a polypeptide, an antibody, or a host cell that is in an environment different from that in which the polynucleotide, nucleic acid, protein, polypeptide, antibody, or host cell naturally occurs. In reference to a sequence, such as nucleic acid or amino acid, "isolated" includes sequences that are assembled, synthesized, amplified, or otherwise engineered by methods known in the art.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide. Preferably, the conditions are such that sequences at least about 65%, 70%, 75%, 85%, 90%, 95%, 98%, or 99% homologous to each other typically remain hybridized to each other.

The term "identity" in the context of sequences refers to the relatedness of two sequences on a nucleotide-by-nucleotide basis or amino acid-by-amino acid basis over a particular comparison window or segment. Thus, identity is defined as the degree of sameness, correspondence, or equivalence between the same strands (either sense or antisense) of two DNA segments or the primary structure of two polypeptides.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. "Identity between two amino acid sequences" is defined as the presence of a series of exactly alike or invariant amino acid residues in both sequences. The percentage of sequence identity is calculated by comparing two optimally aligned sequences over a particular region, determining the number of positions at which the identical base occurs in both sequence in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup, FASTDB (Intelligenetics), BLAST (National Center for Biomedical Information; Altschul et al., Nucleic Acids Research 25:3389 3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (U.S. Pat. No. 5,912,120.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

The terms "homology", "homologous," "substantially similar," and "corresponding substantially" are used interchangeably. They refer to sequence fragments, nucleic acid or amino acid, wherein changes in one or more bases or residues does not affect the ability of the fragment to result in a specific functional protein. These terms also refer to modifications of the nucleic acid or amino acid sequences of the instant invention such as deletion or insertion of one or more nucleotides or residues that do not substantially alter the functional properties of the resulting sequence relative to the initial, unmodified sequence. It is therefore understood, as those skilled in the art will appreciate, that the invention encompasses more than the specific exemplary sequences.

The term "operably linked" or "operatively linked" refers to the association of nucleic acid sequences on a single nucleic acid fragment so that the function of one is regulated by the other or is not hindered by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, two proteins can be operably linked, such that the function of either protein is not compromised. Generally, operably linked means that the nucleic acid sequences being linked are contiguous and, where necessary to join two protein coding regions, contiguous and in the same reading frame.

The term "expression", as used herein, refers to the production of a functional end-product.

By "substantially the same length" is meant that any difference in length does not exceed about 20%, usually does not exceed about 10% and more usually does not exceed about 5%; and have sequence identity to any of these sequences of at least about 80%, 85%, 90%, 95%, and usually at least about 99% over the entire length of the nucleic acid.

The term "polypeptide composition" as used herein refers to both the full-length protein, as well as portions or fragments thereof. Also included in this term are variations of the naturally occurring protein, where such variations are homologous or substantially similar to the naturally occurring protein, and mutants of the naturally occurring proteins, as described herein.

The term "bacteriocin" refers to proteinaceous toxins produced by bacteria to inhibit the growth of similar or closely related bacterial strains.

The term "effective amount" refers to the amount necessary to elicit a change in the environment or solution. For example, an effective amount of bactericidal yeast added to an environment would result in a reduction, elimination, or prevention of contamination.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Nisin Protein Synthesis

Nisin is an antibacterial bacteriocin substance that is secreted by some strains of Lactococcus lactis (L. lactis) bacteria. Nisin A (or nisin Z, which differs by a single amino acid from nisin A) is synthesized as a precursor peptide but then undergoes extensive, covalent, enzymatic modification to become an antibiotic molecule. The antibiotic final form of nisin is secreted by L. lactis to kill competing lactic acid bacteria in their local environment. Nisin is a commercial product used widely in the food and beverage industries. It has Generally Regarded As Safe (GRAS) status under US FDA regulations.

To demonstrate proof of principle for the use of bacteriocins secreted by genetically engineered yeast in protecting against bacterial contamination, the nisin A gene was cloned into the genome of the yeast Kluyveromyces lactis. Because yeast do not have the enzymes necessary to convert nisin peptide into the antibiotic chemical form, it was not anticipated that the nisin A peptide would have antibacterial activity. However, preparations from the nisin A containing yeast were found to have antibacterial activity when tested in a bacterial killing assay. Specifically, nisin A yeast preparations killed the target *Enterococcus faecalis* bacteria in a dose dependent manner, while preparations from non-engineered yeast did not.

The unmodified nisin gene was constructed using oligonucleotides that were commercially synthesized where the nisin peptide open reading frame was flanked with a 5 prime XhoI-Kex cleavage site and a 3 prime StuI site using internal overlapping cohesive ends. The open reading frame of the nisin peptide was codon harmonized according to *Kluyveromyces lactis* codon usage frequency (Table 1, SEQ ID NO. 16). The oligos were annealed, phosphorylated, ligated, and then the single double-stranded molecule was ligated into the commercial pKLAC1 yeast expression vector.

Example 2

General Cloning and Expression of AP Proteins

The antibacterial proteins of the invention were cloned into a yeast expression system and analyzed for antibacterial activity. The commercial yeast expression system (New England Biolabs) for Kluyveromyces lactis with the pKLAC1 shuttle vector was used. An AP to be expressed was cloned into the multiple cloning site of the pKLAC1 plasmid at the XhoI and BGLII restriction sites. The AP codons were placed in frame with both the KEX protease recognition site (amino acids lysine-arginine) and the preceding alpha mating factor secretion peptide so that the yeast would correctly process and secrete the AP. After cloning the AP gene into pKLAC1 in frame, the plasmid was amplified in *E. coli* host cells using ampicillin selection. Extracted plasmid was then linearized with the restriction enzyme SacII, which exposed the DNA sequence homologous with the *K. lactis* LAC4 at both the 5 prime and 3 prime termini of the vector. Specifically, 2 µg of pKLAC1 DNA containing an AP of interest was digested with 20 units of SacII in 50 µl of 1× NE Buffer at 37° C. for 2 hours. The digested DNA was desalted using a commercially available DNA fragment purification kit.

Introduction of the linearized expression cassette into *K. lactis* cells was achieved by chemical transformation using *K. lactis* GG799 Competent Cells and NEB Yeast Transformation Reagent. Specifically, 620 µl of NEB Yeast Transformation Reagent was added to *K. lactis* competent cells on ice. About 1 µg of linearized pKLAC1 DNA containing the AP of interest was added to the cell mixture, which was then incubated at 30° C. for 30 minutes. The cell mixture was heat shocked by incubating it at 37° C. for 1 hour in a water bath. The cells were pelleted by microcentrifugation at about 7000 r.p.m. for 2 minutes and the supernatant was discarded. The cell pellet was resuspended in 1 mL of sterile deionized water. The cells were again microcentrifuged at about 7000 r.p.m. for 2 minutes and the supernatant was discarded. The cells were then resuspended in 1 mL YPGlu medium and transferred to a sterile culture tube and incubated at 30° C. while shaking for 30 minutes. The cells were pelleted by microcentrifugation as described above and resuspended in 1 mL of sterile deionized water. The resuspended cells were plated onto separate YCB Agar Medium plates containing 5 mM acetamide and incubated at 30° C. for 3 to 4 days until colonies formed. Only the yeast that recombined the AP vector sequence into the endogenous LAC4 promoter, via homologous recombination, were able to utilize acetamide as a nitrogen source due to the presence of the acetamidase enzyme transgene in the vector. AP expression was driven by the constitutive expression of the LAC4 gene in the yeast.

Figure 3:
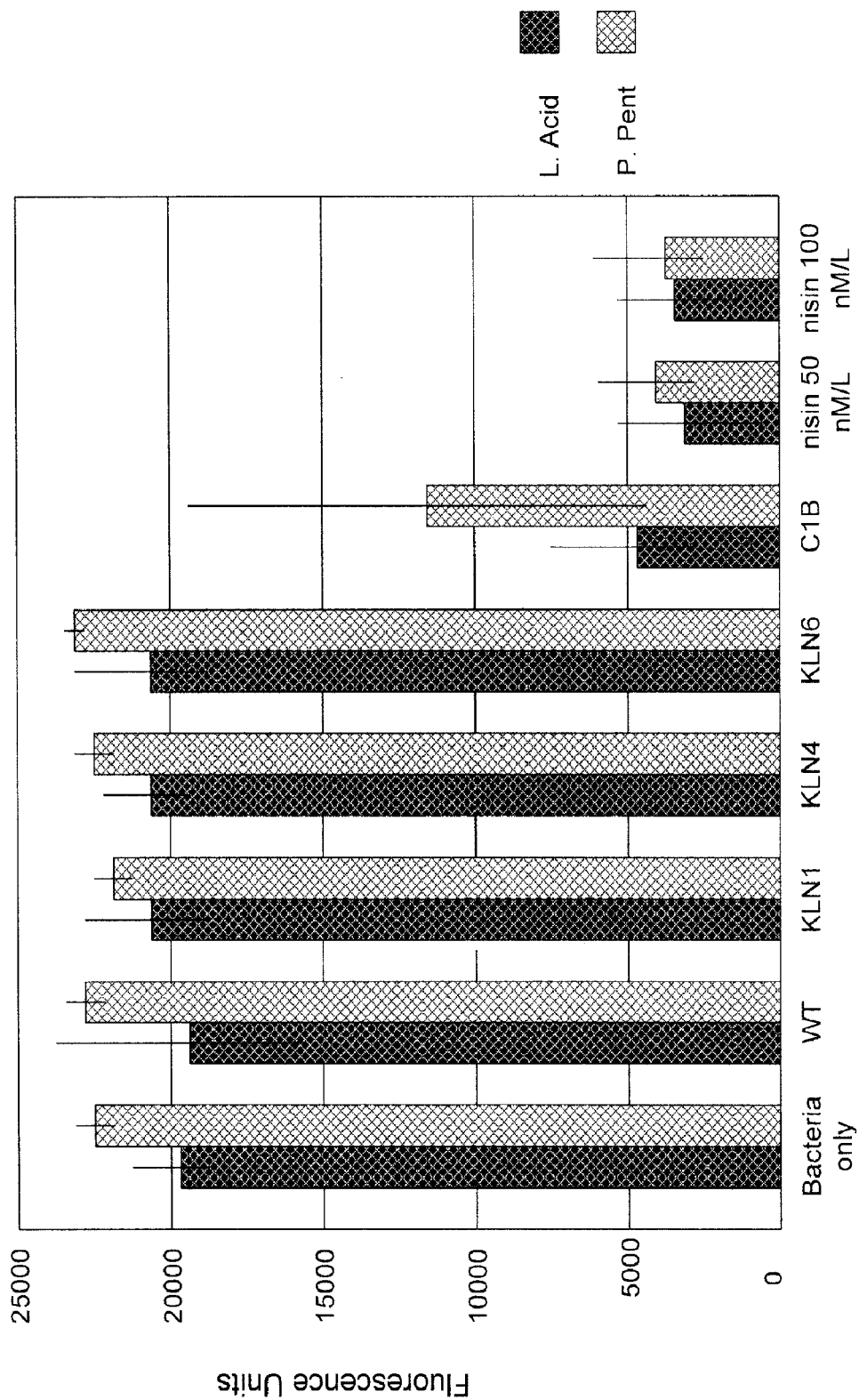
FIG. 3 demonstrates graphic illustration of antibacterial activity in the AP secreting yeast.

To determine if the cloned yeast expressed the inserted AP, supernatants were extracted from three separate yeast colonies. The supernatants were analyzed by Liquid chromatography-mass spectrometry (LC-MS) analysis. The LC/MS chromatograms of three yeast cell supernatants showed that the yeast were expressing the nisin transgene product (FIGS. 2, 3, and 4). The MS peak at 701 indicates the presence of the expressed nisin transgene in the supernatant. The 697 peak is a non-transgenic natural product of the yeast. Further, the small peaks close to 701 are the radioisotope variants that are commonly observed.

Example 3

Antibacterial Activity in AP Secreting Yeast

Antibacterial activity in yeast culture supernatants was tested against 3 target strains of lactic acid bacteria including *Enterococcu faecalis* 32, *Lactobacillus acidophilus* (ATCC), and *Pediococcus pentosaceus*. The method was a modification of the protocol described in Berjeaud et al. Appl Microbiol. Biotechol. 57:757-763, 2001. Each species was transformed with pLSYC02, a plasmid carrying the luxA::B fusion protein controlled by the lactococcal p59 promoter and an erythromycin resistance gene. The luxA:B fusion protein causes luminescent light emission when living bacteria are exposed to nonaldehyde. Killed bacteria do not emit light. Bacteria were grown in phosphate buffered (pH7) Terrific Broth with glycerol containing 150 µg/mL erythromycin (TBG). Single colonies from agar plates were used to seed overnight cultures, which were incubated at 37° C. with shaking. The next day, the cultures were diluted 1:5 in TBG, grown for one hour and then placed on ice. For the antibacterial activity assay, cells were washed in saline and aliquoted $3 \times 10^7$ per well in 50 µL of phosphate buffered saline pH7 into 96 well opaque plates. Next, 50 µL of test supernatant or diluted authentic nisin peptide was added to each well in triplicate. Luminescence was measured in a BMG Lumistar Optima luminometer after three baseline measurements, 1 second integration at a gain of 4000, and injection of 2 µL/well of the bacterial luciferase substrate nonaldehyde. Twenty subsequent measurements were made and luminescence was compared for all wells at the cycle showing peak signal, usually cycle 10 after injection. For negative controls, *K. lactis* supernatants from cells bearing an integrated copy of the empty pKLAC1 expression cassette or expressing the maltose binding protein from the pKLAC1-malE expression cassette (New England Biolabs) were used. For positive controls, nisin reagent (MP Biologicals), or nisin peptide synthesized by Genscript, was used. As shown in FIG. 5, synthetic nisin that had not been modified exhibited antibacterial activity. Contrary to what is known in the art, nisin does not need to be modified to elicit antibacterial activity.

Example 4

Vector Creation

A re-engineered pKS1 plasmid (pKS1-suc) was created by having DNA commercially synthesized that contains the S. cerevisiae invertase enzyme secretory leader peptide sequence suc2, fused to the eight amino acid strep II sequence. The fragment was ligated into the SpeI/BamHI sites of pKS1 (FIG. 2).

The synthetic bacteriocin peptides and lysine enzymes were resynethsized with BamHI 5-prime and SalI or XhoI 3-prime termini for in frame cloning with the suc2 secretory peptide and cleavage site. SEQ ID NO. 16. Additionally, promoter sites were integrated into the vector. SEQ ID NO.

16. In this example a series of six promoter regions taken from the most highly expressed genes of *S. cerevisiae*: PMA1 Plasma membrane H+-ATPase; TDH2 Glyceraldehyde-3-phosphate dehydrogenase, isozyme 2; ILV5 Acetohydroxy-acid reductoisomerase; FBA1 Fructose 1,6-bisphosphate aldolase; DLD1 D-lactate dehydrogenase; CWP2 Covalently linked cell wall mannoprotein were incorporated. These regions comprise approximately 1200 base pairs immediately 5-prime of the transcription start site for the given genes. The exact sequences were determined by promoter analysis using the UCSC Genome Browser. The promoter sequences have SacI 5-prime and SpeI 3-prime sites to allow substitution of the ADH2 promoter of pKS1. At the 5-prime end, just after the SacI site, and EcoRI site was added. Then a spacer sequence of 20 random base pairs (to promote efficient cutting) will precede a PstI. That PstI site was used to target the PstI site at position 2952 for directional cloning when the vector is converted to the integrating type. The natural 5' prime promoter sequence will follow the PstI site for 300-600 base pairs. Then midway in the promoter, the restriction sites XbaI followed by EcoRI was inserted. The EcoRI site was followed by the remaining 3-prime portion of the promoter, also comprising 300-600 base pairs. Insertion of the recombinant protein leaves only one PstI site in the plasmid, just outside of the G418 selection gene.

To convert the vector from the plasmid type to the integrating type, the following steps were taken: i) the plasmid was cut with EcoRI and the two fragments were separated and collected by gel electrophoresis; ii) the cut plasmid were re-circularized by ligating the two EcoRI ends together. This left the 3-prime promoter region intact relative to the transcription start site; iii) then the 5-prime promoter fragment and the re-circularized plasmid were cut with PstI and XbaI, and these two fragments were joined in a directional ligation reaction. Inserting the PstI/XbaI promoter fragment destroyed the DNA that controls plasmid replication in yeast, but the DNA required for replication and selection in *E. coli* remained intact, so the resulting pSK1-suc was a viable shuttle vector.

Using the shuttle vector *S. cerevisiae*, can be transformed. The new shuttle vector (pSK1-suc) need only be cut with XbaI and SacI, removing the *E. coli* related DNA, and generating a linear piece of double stranded DNA whose 5-prime and 3-prime ends are perfectly homologous with the endogenous promoter of the selected gene. *S. cerevisiae* cells can then be made chemically competent using the Zymo Research kit and transformed with the linear fragment. Then using the same DNA repair mechanism as with the pKLAC1 vector in *K. lactis*, the fragment should become integrated into the endogenous promoter, creating a hybrid promoter (part from the vector, part from the chromosome) of completely correct sequence to drive expression of the transgenic protein, and a similarly hybrid promoter to drive expression of the endogenous gene in situ. The transformed yeast produced can then be used for further testing to confirm the desired antibacterial properties.

Example 5

Antibacterial Activity in AP Secreting Yeast

Antibacterial activity or bacteria growth inhibition was determined in yeast culture where bacteriocins are integrated into the genome. Further, concentrations of nisin were also tested to determine the antibacterial activity.

The test reviewed eight (8) different examples including: bacteria only: bacteria with no yeast; WT: unmodified *Kluyveromyces lactis* yeast cells. KLN1, KLN4, KLN6: three different clones of *K. lactis* with the same expression cassette for nisin peptide integrated into the genome; C1B: one *K. lactis* clone with an expression cassette for a mundticin-like bacteriocin integrated into the genome; nisin: nisin component concentration of a commercial nisin preparation. (See FIG. 3)

An amount of 20 lactic acid bacteria cells containing an erythromycin resistance plasmid were added to each well of a 48 well microplate, containing zero or 10,000 yeast cells, 10 µg/ml erythromycin, and 0.5 ml yeast peptone medium with 2% galactose. Cells were grown 8-10 hours at 30 degrees C. with vigorous shaking. 100 µl samples from each well were then transferred to 200 µl tubes and centrifuged to pellet all cells. After removing the supernatant, 100 µl of water containing 5 µM/L Syto 9 (Invitrogen Cat. No. S-34854) was added, and cell pellets were resuspended and transferred to a 96 well Fluodia fluorescence plate reader (Photon Technology Inc). The fluorescence was then measured using FITC excitation and emission filters. The assays were completed in triplicate with the results provided in FIG. 3 (Bacteria species: L. Acid=*Lactobacillus acidophilus*; P. Pen=*Pediococcus pentosaceus*)

As can be seen from the results the yeast culture that contained an amount of the bacteriocin or nisin compound demonstrated a marked reduction in fluorescence, which can be correlated to the breakdown of the cellular walls of the lactic acid bacteria cells and thus bacteria inhibition or antibacterial activity.

Example 6

Ethanol Inducible System

Methods to control lactic acid bacterial growth during fermentation include using inducible promoter systems. One such system that may be employed is the alcohol dehydrogenase I promoter system derived from Aspergillus nidulans.

The alcohol dehydrogenase I promoter system consists of two DNA sequence components. The first component consists of the following DNA sequences, fused together, in five prime to three prime order: 1) the alcohol dehydrogenase I promoter of Aspergillus nidulans (derived from Genbank M16916.1) containing the alcA binding site for the alcR transcription factor, 2) a yeast signal peptide sequence to mediate secretion of the gene product; 3) the open reading frame of the gene for any of bacteriocins, such as, but not limited to, nisin or those encoded by SEQ ID NOs: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO 9, SEQ ID NO 10, SEQ ID NO 11 or SEQ ID NO 12 a cell wall-associated protein domain specific to bacteria of the order Lactobacillaceae derived from the cell wall lytic enzyme genes of phages that infect lactic acid bacteria. The second sequence component consists of the following DNA sequences, fused together, in five prime to three prime order: 1) a constitutive promoter such as SV40; 2) an open reading frame for the alcR transcription factor protein that is derived from the gene of that function in *Asperigillus nidulans*. The two DNA sequence components may be synthesized using oligonucleotides with overlapping cohesive ends. The two DNA sequence components may be codon harmonized according to the codon usage frequency for the desired host to optimize expression properties.

In this system, the transcription factor transgene, alcR, will be constitutively expressed. When ethanol is present in the environment, the alcR transcription factor will activate transcription of the transgenic enzyme and the transgenic host cells will synthesize and secrete the lytic enzymes that are targeted to competitive bacteria in the environment.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

What is claimed is:

1. An isolated cell that expresses at least one antibacterial protein having a nucleic acid sequence comprising SEQ ID NO: 1, wherein the isolated cell that expresses at least one antibacterial protein is a yeast cell that is selected from the group consisting of *Kluyveromyces lactis, Saccharomyces cerevisiae, Schizosaccharomyces pombe*, and *Candida albicans*.

2. An isolated microscopic transgenic eukaryotic organism, wherein the isolated microscopic transgenic eukaryotic organism expresses at least one antibacterial protein having a nucleic acid sequence comprising SEQ ID NO: 1.

3. The isolated microscopic transgenic eukaryotic organism of claim 2, wherein the antibacterial protein is expressed in response to lactic acid.

4. The isolated microscopic transgenic eukaryotic organism of claim 2, wherein the antibacterial protein is expressed in response to ethanol.

5. The isolated microscopic transgenic eukaryotic organism of claim 2, wherein the organism is a yeast strain.

6. The isolated microscopic transgenic eukaryotic organism of claim 5, wherein the yeast strain is selected from the group consisting of *Kluyveromyces lactis, Saccharomyces cerevisiae, Schizosaccharomyces pombe*, and *Candida albicans*.

7. An isolated bactericidal yeast, wherein the isolated bactericidal yeast expresses at least one antibacterial protein having a nucleic acid sequence comprising SEQ ID NO: 1.

8. The isolated bactericidal yeast of claim 7, wherein the isolated bactericidal yeast is selected from the group consisting of *Kluyveromyces lactis, Saccharomyces cerevisiae, Schizosaccharomyces pombe*, and *Candida albicans*.

9. The isolated bactericidal yeast of claim 7, wherein the antibacterial protein is expressed in response to lactic acid.

10. The isolated bactericidal yeast of claim 7, wherein the antibacterial protein is expressed in response to ethanol.

11. A method of protecting against bacterial contamination, the method comprising adding an effective amount of bactericidal yeast to an environment to be protected, wherein the bactericidal yeast express at least one antibacterial protein having a nucleic acid sequence comprising SEQ ID NO: 1.

12. The method of claim 11, wherein the antibacterial protein is expressed in the presence of lactic acid.

13. The method of claim 11, wherein the antibacterial protein is expressed in response to ethanol.

14. A method of protecting against bacterial contamination of a batch solution comprising: a. preparing a batch solution; and, b. adding an effective amount of transgenic yeast to the batch solution, wherein the transgenic yeast express an antibacterial protein, and further wherein the antibacterial protein expressed by the transgenic yeast has a nucleic acid sequence comprising SEQ ID NO: 1.

15. The method of claim 14, wherein the antibacterial protein is expressed in the presence of lactic acid.

16. The method of claim 14, wherein the antibacterial protein is expressed in response to ethanol.

* * * * *

SEQUENCE LISTING

<160> NUMBER OF SEQ ID NOS: 27

<210> SEQ ID NO 1
<211> LENGTH: 769
<212> TYPE: DNA
<213> ORGANISM: Artificial
<220> FEATURE:
<223> OTHER INFORMATION: Synthetic Nisin Gene Cloned
<220> FEATURE:
<221> NAME/KEY: misc_feature
<222> LOCATION: (762)..(762)
<223> OTHER INFORMATION: n is a, c, g, or t

<400> SEQUENCE: 1
aaactgacat cgacgatctt ccaatatcgg ttccagaaga agccttgatt ggattcattg      60
acttaaccgg ggatgaagtt tccttgttgc ctgttaataa cggaacccac actggtattc     120
tattcttaaa caccaccatc gctgaagctg ctttcgctga caaggatgat ctcgagaaaa     180
gaatgattac ttctatttct ttgtgtactc caggttgtaa aactggtgct ttgatgggtt     240
gtaatatgaa aactgctact tgtcattgtt ctattcatgt ttctaaataa aggccttgaa     300
tcgagaattt atacttagat aagtatgtac ttacaggtat atttctatga gatactgatg     360
tatacatgca tgataatatt taaacggtta ttagtgccga ttgtcttgtc cgataatgac     420
gttcctatca aagcaataca cttaccacct attacatggg ccaagaaaat attttcgaac     480
ttgtttagaa tattagcaca gagtatatga tgatatccgt tagattatgc atgattcatt     540
cctacaactt tttcgtagca taaggattaa ttacttggat gccaataaaa aaaaaaaaca     600
tcgagaaaat ttcagcatgt cagaaacaat tgcagtgtat caaagtaaaa aaaagatttt     660
cactacatgt tccttttgaa gaaagaaaat catggaacat tagatttaca aaaatttaac     720
caccgctgat taaccgatta gaccgttaag cgcacaacag gnttattag                 769

<210> SEQ ID NO 2
<211> LENGTH: 227
<212> TYPE: DNA
<213> ORGANISM: Artificial
<220> FEATURE:
<223> OTHER INFORMATION: C1A ORF 210

<400> SEQUENCE: 2
ctcgagaaaa gaatgtataa ggaattaact gtagatgaat tagctttgat tgacggtggt      60
aaaaagaaga agaagaaagt tgcttgtact tggggtaatg ctgcaactgc cgcagcttcc     120
ggagctgtga aaggtatttt aggtggtcca accggtgcct tggcaggagc tatttggggt     180
gtttcccagt gtgcttccaa taacttacat ggtatgcatt aaagatc                   227

<210> SEQ ID NO 3
<211> LENGTH: 155
<212> TYPE: DNA
<213> ORGANISM: Artificial

```
<220> FEATURE:
<223> OTHER INFORMATION: C1B ORF 139

<400> SEQUENCE: 3
ctcgagaaga gaatggctac cagatcatac ggtaacggtg tgtactgtaa taattctaaa      60
tgttgggtga attggggtga acccaaccag aatattgccg gtatagtgat ctctggttgg     120
gctagtggat tggcaggtat gggtcattaa agatc                                155

<210> SEQ ID NO 4
<211> LENGTH: 143
<212> TYPE: DNA
<213> ORGANISM: Artificial
<220> FEATURE:
<223> OTHER INFORMATION: C1C ORF 118

<400> SEQUENCE: 4
ctcgagaaga gaatgaaata ttatggtaac ggagtacatt gtactaagtc tggatgttct      60
gttaattggg gtgaagcttt ctctgctggt gtacatagac ttgccaatgg tggtaacggt     120
ttttggtaaa gatcttagac gcg                                             143

<210> SEQ ID NO 5
<211> LENGTH: 229
<212> TYPE: DNA
<213> ORGANISM: Artificial
<220> FEATURE:
<223> OTHER INFORMATION: C2A ORF 214

<400> SEQUENCE: 5
ctcgagaaaa gaatggcaaa ggaatttggt attgctgctg tgtcgccggt accgttttga      60
acgtcgttga agctggaggt tgggttacaa ctattgtatc tatttttgacc gccgtaggta    120 gtggtggttt gtctttgctt gccgctgctg gtagagaatc tatcaaagct tatttgaaga    180
aggaaatcaa gaagaaagga aaaagagctg tcatagcctg gtaaagatc                229

<210> SEQ ID NO 6
<211> LENGTH: 229
<212> TYPE: DNA
<213> ORGANISM: Artificial
<220> FEATURE:
<223> OTHER INFORMATION: C2B ORF 136

<400> SEQUENCE: 6
ctcgagaaaa gaatggcaaa ggaatttggt attgctgctg tgtcgccggt accgttttga      60
acgtcgttga agctggaggt tgggttacaa ctattgtatc tatttttgacc gccgtaggta    120 gtggtggttt gtctttgctt gccgctgctg gtagagaatc tatcaaagct tatttgaaga    180
aggaaatcaa gaagaaagga aaaagagctg tcatagcctg gtaaagatc                229

<210> SEQ ID NO 7
<211> LENGTH: 250
<212> TYPE: DNA
<213> ORGANISM: Artificial
<220> FEATURE:
<223> OTHER INFORMATION: Enterocin-like

<400> SEQUENCE: 7
actagtaaaa atgatgcttt tgcaagctttt ccttttcctt ttggctggtt ttgcagccaa     60
aatatctgca tctatgatgt ggagccaccc gcagttcgaa aaaggatcca tgggcgctat    120
cgcaaagttg gttgctaagt ttggttggcc aatagtcaag aaatactata agcagattat    180
gcaattcatc gggggaaggat gggccattaa caaaatcata gattggatta agaaacatat    240
```

```
ctaactcgag                                                          250

<210> SEQ ID NO 8
<211> LENGTH: 268
<212> TYPE: DNA
<213> ORGANISM: Artificial
<220> FEATURE:
<223> OTHER INFORMATION: Mundticin-like

<400> SEQUENCE: 8
actagtaaaa atgatgcttt tgcaagcttt ccttttcctt ttggctggtt ttgcagccaa     60
aatatctgca tctatgatgt ggagccaccc gcagttcgaa aaggatcca tgagtcaagt    120 tgtaggtgga agtactatg gtaatggtgt ctcttgcaac aagaaaggct gttccgttga    180
ttggggcaag gccataggaa tcattggtaa caactcagca gctaatcttg ccacaggcgg    240
ggcagctggt tggaaatcat aactcgag                                      268

<210> SEQ ID NO 9
<211> LENGTH: 237
<212> TYPE: DNA
<213> ORGANISM: Artificial
<220> FEATURE:
<223> OTHER INFORMATION: Baca-like

<400> SEQUENCE: 9
ggatccatga agaagaaagt attgaaacac tgtgttattc taggtattct tgggacttgc     60
ttagcaggta taggaaccgg catcaaagtc gatgctgcta catactacgg caacggattg    120
tattgtaaca agagaagtg ttgggtggat tggaatcaag ccaagggaga atcggcaag     180 attatcgtta acggttgggt taatcatggt ccttgggcgc aagaagata actcgag       237

<210> SEQ ID NO 10
<211> LENGTH: 216
<212> TYPE: DNA
<213> ORGANISM: Artificial
<220> FEATURE:
<223> OTHER INFORMATION: 33613 py117 Plasmid Bacteriocin-like

<400> SEQUENCE: 10
ggatccatga agaagaaact cgtcatttgc ggcattatcg gtatcggatt cactgcattg     60
ggcacaaacg ttgaagcagc cacctattac ggtaatggtc tttactgtaa caaacaaaag    120
tgttgggttg attggaacaa agcttctaga gagattggaa agataatcgt gaatggctgg    180
gtacaacatg gaccatgggc tcctagataa ctcgag                             216

<210> SEQ ID NO 11
<211> LENGTH: 250
<212> TYPE: DNA
<213> ORGANISM: Artificial
<220> FEATURE:
<223> OTHER INFORMATION: 33608 Nisin Peptide with 5-Prime Strep II Tag

<400> SEQUENCE: 11
atgtggagcc acccgcagtt cgaaaaaact agtaaaaatg atgcttttgc aagcttttcct    60 tttccttttg ctggttttg cagccaaaat atctgcatct atgatgtgga gccacccgca    120
gttcgaaaaa ggatccatga taacttccat cagtttatgt acgccaggtt gcaagacagg    180
agctttgatg ggctgtaaca tgaaaacagc aacttgcaat tgttctattc atgtttcaaa    240
ataactcgag                                                          250
```

<210> SEQ ID NO 12
<211> LENGTH: 161
<212> TYPE: DNA
<213> ORGANISM: Artificial
<220> FEATURE:
<223> OTHER INFORMATION: C1A ORF 210

<400> SEQUENCE: 12

```
ctcgagaaaa gaatgggtgg taagtactat ggtaacggag ttacctgtgg taagcatagt      60
tgttcagttg attggggtaa agcaacaaca tgtataatta ataacggtgc tatggcctgg     120
ccaaccggag gtcatcaagg taatcataag tgttgaagat c                         161
```

<210> SEQ ID NO 13
<211> LENGTH: 235
<212> TYPE: PRT
<213> ORGANISM: Artificial
<220> FEATURE:
<223> OTHER INFORMATION: Synthetic Nisin Gene Cloned

<400> SEQUENCE: 13

```
Asn His Arg Arg Ser Ser Asn Ile Gly Ser Arg Arg Ser Leu Asp Trp
1               5                   10                  15

Ile His Leu Asn Arg Gly Ser Phe Leu Val Ala Cys Arg Asn Pro His
            20                  25                  30

Trp Tyr Ser Ile Leu Lys His His Arg Ser Cys Phe Arg Gln Gly
    35                  40                  45

Ser Arg Glu Lys Asn Asp Tyr Phe Tyr Phe Val Tyr Ser Arg Leu
    50                  55                  60

Asn Trp Cys Phe Asp Gly Leu Tyr Glu Asn Cys Tyr Leu Ser Leu Phe
65                  70                  75                  80

Tyr Ser Cys Phe Ile Lys Ala Leu Asn Arg Glu Phe Ile Leu Arg Val
                85                  90                  95

Cys Thr Tyr Arg Tyr Ile Ser Met Arg Tyr Cys Ile His Ala Tyr Leu
            100                 105                 110

Asn Gly Tyr Cys Arg Leu Ser Cys Ala Ile Met Thr Phe Leu Ser Lys
        115                 120                 125

Gln Tyr Thr Tyr His Leu Leu His Gly Pro Arg Lys Tyr Phe Arg Thr
    130                 135                 140

Cys Leu Glu Tyr His Arg Val Tyr Asp Asp Ile Arg Ile Met His Asp
145                 150                 155                 160

Ser Phe Leu Gln Leu Phe Arg Ser Ile Arg Ile Asn Tyr Leu Asp Ala
                165                 170                 175

Asn Lys Lys Lys Lys His Arg Glu Asn Phe Ser Met Leu Arg Asn Asn
            180                 185                 190

Cys Ser Val Ser Lys Lys Lys Asp Phe His Tyr Met Phe Leu Leu Lys
        195                 200                 205

Lys Glu Asn His Gly Thr Leu Asp Leu Gln Lys Phe Asn His Arg Leu
    210                 215                 220

Thr Asp Thr Val Lys Arg Thr Thr Gly Leu Leu
225                 230                 235
```

<210> SEQ ID NO 14
<211> LENGTH: 75
<212> TYPE: PRT
<213> ORGANISM: Artificial
<220> FEATURE:
<223> OTHER INFORMATION: C1A ORF 210

<400> SEQUENCE: 14

```
Leu Glu Lys Arg Met Tyr Lys Glu Leu Thr Val Asp Glu Leu Ala Leu
1               5                   10                  15

Ile Asp Gly Gly Lys Lys Lys Lys Val Ala Cys Thr Trp Gly
            20                  25                  30

Asn Ala Ala Thr Ala Ala Ala Ser Gly Ala Val Lys Gly Ile Leu Gly
                35                  40                  45

Gly Pro Thr Gly Ala Leu Ala Gly Ala Ile Trp Gly Val Ser Gln Cys
        50                  55                  60

Ala Ser Asn Asn Leu His Gly Met His Arg Ser
65                  70                  75
```

<210> SEQ ID NO 15
<211> LENGTH: 51
<212> TYPE: PRT
<213> ORGANISM: Artificial
<220> FEATURE:
<223> OTHER INFORMATION: C1B PRF 139

<400> SEQUENCE: 15

```
Leu Glu Lys Arg Met Ala Thr Arg Ser Tyr Gly Asn Gly Val Tyr Cys
1               5                   10                  15

Asn Asn Ser Lys Cys Trp Val Asn Trp Gly Glu Ala Lys Gln Asn Ile
            20                  25                  30

Ala Gly Ile Val Ile Ser Gly Trp Ala Ser Gly Leu Ala Gly Met Gly
                35                  40                  45

His Arg Ser
    50
```

<210> SEQ ID NO 16
<211> LENGTH: 46
<212> TYPE: PRT
<213> ORGANISM: Artificial
<220> FEATURE:
<223> OTHER INFORMATION: C1C ORF 118

<400> SEQUENCE: 16

```
Leu Glu Lys Arg Met Lys Tyr Tyr Gly Asn Gly Val His Cys Thr Lys
1               5                   10                  15

Ser Gly Cys Ser Val Asn Trp Gly Glu Ala Phe Ser Ala Gly Val His
            20                  25                  30

Arg Leu Ala Asn Gly Gly Asn Gly Phe Trp Arg Ser Thr Arg
                35                  40                  45
```

<210> SEQ ID NO 17
<211> LENGTH: 76
<212> TYPE: PRT
<213> ORGANISM: Artificial
<220> FEATURE:
<223> OTHER INFORMATION: C2A ORF 214

<400> SEQUENCE: 17

```
Leu Glu Lys Arg Met Ala Lys Glu Phe Gly Ile Pro Ala Ala Val Ala
1               5                   10                  15

Gly Thr Val Leu Asn Val Val Glu Ala Gly Gly Trp Val Thr Thr Ile
            20                  25                  30

Val Ser Ile Leu Thr Ala Val Gly Ser Gly Gly Leu Ser Leu Leu Ala
                35                  40                  45

Ala Ala Gly Arg Glu Ser Ile Lys Ala Tyr Leu Lys Lys Glu Ile Lys
        50                  55                  60

Lys Lys Gly Lys Arg Ala Val Ile Ala Trp Arg Ser
65                  70                  75
```

-continued

```
<210> SEQ ID NO 18
<211> LENGTH: 50
<212> TYPE: PRT
<213> ORGANISM: Artificial
<220> FEATURE:
<223> OTHER INFORMATION: C2B ORF 136

<400> SEQUENCE: 18

Leu Glu Lys Arg Met Gly Lys Tyr Tyr Gly Asn Gly Val His Cys Gly
1               5                   10                  15

Lys His Ser Cys Ser Val Asp Trp Gly Lys Ala Ile Gly Ile Ile Gly
            20                  25                  30

Asn Asn Ala Ala Ala Asn Trp Ala Thr Gly Gly Asn Ala Gly Trp Lys
        35                  40                  45

Arg Ser
    50

<210> SEQ ID NO 19
<211> LENGTH: 53
<212> TYPE: PRT
<213> ORGANISM: Artificial
<220> FEATURE:
<223> OTHER INFORMATION: C2C ORF 145

<400> SEQUENCE: 19

Leu Glu Lys Arg Met Gly Gly Lys Tyr Tyr Gly Asn Gly Val Thr Cys
1               5                   10                  15

Gly Lys His Ser Cys Ser Val Asp Trp Gly Lys Ala Thr Thr Cys Ile
            20                  25                  30

Ile Asn Asn Gly Ala Met Ala Trp Ala Thr Gly Gly His Gln Gly Asn
        35                  40                  45

His Lys Cys Arg Ser
    50

<210> SEQ ID NO 20
<211> LENGTH: 6745
<212> TYPE: DNA
<213> ORGANISM: Artificial
<220> FEATURE:
<223> OTHER INFORMATION: pks1-suc2/ST

<400> SEQUENCE: 20
caatacgcaa accgcctctc cccgcgcgtt ggccgattca ttaatgcagc tggcacgaca      60
ggagctcaaa acgtaggggc aaacaaacgg aaaaatcgtt tctcaaattt tctgatgcca     120
agaactctaa ccagtcttat ctaaaaattg ccttatgatc cgtctctccg gttacagcct     180
gtgtaactga ttaatcctgc ctttctaatc accattctaa tgttttaatt aagggatttt     240
gtcttcatta acggctttcg ctcataaaaa tgttatgacg ttttgcccgc aggcgggaaa     300
ccatccactt cacgagactg atctcctctg ccggaacacc gggcatctcc aacttataag     360
ttggagaaat aagagaattt cagattgaga gaatgaaaaa aaaaaaaaaa aaaggcagag     420
gagagcatag aaatggggtt cacttttttgg taaagctata gcatgccta t cacatataaa     480 tagagtgcca gtagcgactt ttttcacact cgaaatactc ttactactgc tctcttgttg     540
tttttatcac ttcttgtttc ttcttggtaa atagaatatc aagctacaaa agcatacaa     600 tcaactatca actattaact atatcgtaat actagtaaaa atgatgcttt tgcaagcttt     660
ccttttcctt ttggctggtt ttgcagccaa aatatctgca tctatgatgt ggagccaccc     720
gcagttcgaa aaaggatccc ccgggctgca ggaattcgat atcaagctta tcgataccgt     780
```

```
cgacctcgag tcatgtaatt agttatgtca cgcttacatt cacgccctcc ccccacatcc      840
gctctaaccg aaaaggaagg agttagacaa cctgaagtct aggtccctat ttattttttt      900
atagttatgt tagtattaag aacgttattt atatttcaaa tttttctttt ttttctgtac      960
agacgcgtgt acgcatgtaa cattatactg aaaaccttgc ttgagaaggt tttgggacgc     1020
tcgaaggctt taatttgcgg ccggtaccca attcgcccta tagtgagtcg tattacgcgc     1080
gctcactggc cgtcgtttta caacgtcgtg actgggaaaa ccctggcgtt acccaactta     1140
atcgccttgc agcacatccc cctttcgcca gctggcgtaa tagcgaagag gcccgcaccg     1200 atcgccctttc ccaacagttg cgcagcctga atggcgaatg gacgcgccct gtagcggcgc     1260
attaagcgcg gcgggtgtgg tggttacgcg cagcgtgacc gctacacttg ccagcgccct     1320
agcgcccgct cctttcgctt tcttcccttc ctttctcgcc acgttcgccg ctttccccg      1380 tcaagctcta atcgggggc tccctttagg gttccgattt agtgctttac ggcacctcga     1440
ccccaaaaaa cttgattagg gtgatggttc acgtagtggg ccatcgccct gatagacggt     1500
ttttcgccct ttgacgttgg agtccacgtt ctttaatagt ggactcttgt tccaaactgg     1560
aacaacactc aaccctatct cggtctattc ttttgattta aagggatttt gccgatttc      1620 ggcctattgg ttaaaaaatg agctgattta caaaaattt aacgcgaatt ttaacaaaat     1680
attaacgttt acaatttcct gatgcggtat tttctcctta cgcatctgtg cggtatttca     1740
caccgcatag ggtaataact gatataatta aattgaagct ctaatttgtg agtttagtat     1800
acatgcattt acttataata cagttttctgg atggcggcgt tagtatcgaa tcgacagcag     1860
tatagcgacc agcattcaca tacgattgac gcatgatatt actttctgcg cacttaactt     1920
cgcatctggg cagatgatgt cgaggcgaaa aaaaatataa atcacgctaa catttgatta     1980
aaatagaaca actacaatat aaaaaaacta tacaaatgac aagttcttga aaacaagaat     2040 cttttttattg tcagtactga ttagaaaaac tcatcgagca tcaaatgaaa ctgcaattta     2100
ttcatatcag gattatcaat accatatttt tgaaaaagcc gtttctgtaa tgaaggagaa     2160
aactcaccga gcagttcca taggatggca agatcctggt atcggtctgc gattccgact     2220
cgtccaacat caatacaacc tattaatttc ccctcgtcaa aaataaggtt atcaagtgag     2280
aaatcaccat gagtgacgac tgaatccggt gagaatggca aaagcttatg catttctttc     2340
cagacttgtt caacaggcca gccattacgc tcgtcatcaa aatcactcgc atcaaccaaa     2400
ccgttattca ttcgtgattg cgcctgagcg agacgaaata cgcgatcgct gttaaaagga     2460
caattacaaa caggaatcga atgcaaccgg cgcaggaaca ctgccagcgc atcaacaata     2520
ttttcacctg aatcaggata ttcttctaat acctggaatg ctgttttgcc ggggatcgca     2580
gtggtgagta accatgcatc atcaggagta cggataaaat gcttgatggt cggaagaggc     2640
ataaattccg tcagccagtt tagtctgacc atctcatctg taacatcatt ggcaacgcta     2700
cctttgccat gtttcagaaa caactctggc gcatcgggct tcccatacaa tcgatagatt     2760
gtcgcacctg attgcccgac attatcgcga gcccatttat acccatataa atcagcatcc     2820
atgttggaat ttaatcgcgg cctcgaaacg tgagtctttt ccttacccat ggttgtttat     2880
gttcggatgt gatgtgagaa ctgtatccta gcaagatttt aaaaggaagt atatgaaaga     2940
agaacctcag tggcaaatcc taaccttta tatttctcta caggggcgcg gcgtggggac     3000
aattcaacgc gtctgtgagg ggagcgtttc cctgctcgca ggtctgcagc gaggagccgt     3060
aatttttgct tcgcgccgtg cggccatcaa aatgtatgga tgcaaatgat tatacatggg     3120
gatgtatggg ctaaatgtac gggcgacagt cacatcatgc ccctgagctg cgcacgtcaa     3180
```

```
gactgtcaag gagggtattc tgggccttgg tatggtgcac tctcagtaca atctgctctg   3240
atgccgcata gttaagccag ccccgacacc cgccaacacc cgctgacgcg ccctgacggg   3300
cttgtctgct cccggcatcc gcttacagac aagctgtgac cgtctccggg agctgcatgt   3360
gtcagaggtt ttcaccgtca tcaccgaaac gcgcgagacg aaagggcctc gtgatacgcc   3420 tattttata ggttaatgtc atgataataa tggtttctta gtatgatcca atatcaaagg    3480
aaatgatagc attgaaggat gagactaatc caattgagga gtggcagcat atagaacagc   3540
taaagggtag tgctgaagga agcatacgat accccgcatg gaatgggata atatcacagg   3600
aggtactaga ctacctttca tcctacataa atagacgcat ataagtacgc atttaagcat   3660
aaacacgcac tatgccgttc ttctcatgta tatatatata caggcaacac gcagatatag   3720
gtgcgacgtg aacagtgagc tgtatgtgcg cagctcgcgt tgcattttcg gaagcgctcg   3780
ttttcggaaa cgctttgaag ttcctattcc gaagttccta ttctctagaa agtataggaa   3840
cttcagagcg cttttgaaaa ccaaaagcgc tctgaagacg cactttcaaa aaccaaaaa    3900 cgcaccggac tgtaacgagc tactaaaata ttgcgaatac cgcttccaca aacattgctc   3960
aaaagtatct ctttgctata tatctctgtg ctatatccct ataaccta cccatccacc     4020 tttcgctcct tgaacttgca tctaaactcg acctctacat tttttatgtt tatctctagt   4080
attactcttt agacaaaaaa attgtagtaa gaactattca tagagtgaat cgaaaacaat   4140
acgaaaatgt aaacatttcc tatacgtagt atatagagac aaaatagaag aaaccgttca   4200
taattttctg accaatgaag aatcatcaac gctatcactt tctgttcaca agtatgcgc    4260 aatccacatc ggtatagaat ataatcgggg atgcctttat cttgaaaaaa tgcacccgca   4320
gcttcgctag taatcagtaa acgcgggaag tggagtcagg cttttttat ggaagagaaa    4380 atagacacca aagtagcctt cttctaacct taacggacct acagtgcaaa aagttatcaa   4440
gagactgcat tatagagcgc acaaggaga aaaaagtaa tctaagatgc tttgttagaa     4500
aaatagcgct ctcgggatgc attttttgtag aacaaaaaag aagtatagat tctttgttgg   4560
taaaatagcg ctctcgcgtt gcatttctgt tctgtaaaaa tgcagctcag attcttttgtt  4620 tgaaaaatta gcgctctcgc gttgcatttt tgttttacaa aaatgaagca cagattcttc   4680
gttggtaaaa tagcgctttc gcgttgcatt tctgttctgt aaaaatgcag ctcagattct   4740
ttgtttgaaa aattagcgct ctcgcgttgc attttttgttc tacaaaatga agcacagatg   4800
cttcgttcag gtggcacttt tcggggaaat gtgcgcggaa cccctatttg tttatttttc   4860
taaatacatt caaatatgta tccgctcatg agacaataac cctgataaat gcttcaataa   4920
tattgaaaaa ggaagagtat gagtattcaa catttccgtg tcgcccttat tccctttttt   4980
gcggcatttt gccttcctgt ttttgctcac ccagaaacgc tggtgaaagt aaaagatgct   5040
gaagatcagt tgggtgcacg agtgggttac atcgaactgg atctcaacag cggtaagatc   5100
cttgagagtt ttcgccccga agaacgtttt ccaatgatga gcacttttaa agttctgcta   5160
tgtggcgcgg tattatcccg tattgacgcc gggcaagagc aactcggtcg ccgcatacac   5220
tattctcaga atgacttggt tgagtactca ccagtcacag aaaagcatct tacggatggc   5280
atgacagtaa gagaattatg cagtgctgcc ataaccatga gtgataacac tgcggccaac   5340
ttacttctga caacgatcgg aggaccgaag gagctaaccg cttttttgca caacatgggg   5400
gatcatgtaa ctcgccttga tcgttgggaa ccggagctga atgaagccat accaaacgac   5460
gagcgtgaca ccacgatgcc tgtagcaatg gcaacaacgt tgcgcaaact attaactggc   5520
gaactactta ctctagcttc ccggcaacaa ttaatagact ggatggaggc ggataaagtt   5580
```

| | | |
|---|---|---|
| gcaggaccac ttctgcgctc ggcccttccg gctggctggt ttattgctga taaatctgga | 5640 |
| gccggtgagc gtgggtctcg cggtatcatt gcagcactgg ggccagatgg taagccctcc | 5700 |
| cgtatcgtag ttatctacac gacggggagt caggcaacta tggatgaacg aaatagacag | 5760 |
| atcgctgaga taggtgcctc actgattaag cattggtaac tgtcagacca agtttactca | 5820 |
| tatatacttt agattgattt aaacttcat ttttaattta aaaggatcta ggtgaagatc | 5880 |
| cttttttgata atctcatgac caaaatccct taacgtgagt tttcgttcca ctgagcgtca | 5940 |
| gaccccgtag aaaagatcaa aggatcttct tgagatcctt ttttttctgcg cgtaatctgc | 6000 |
| tgcttgcaaa caaaaaaacc accgctacca gcggtggttt gtttgccgga tcaagagcta | 6060 |
| ccaactcttt ttccgaaggt aactggcttc agcagagcgc agataccaaa tactgtcctt | 6120 |
| ctagtgtagc cgtagttagg ccaccacttc aagaactctg tagcaccgcc tacatacctc | 6180 |
| gctctgctaa tcctgttacc agtggctgct gccagtggcg ataagtcgtg tcttaccggg | 6240 |
| ttggactcaa gacgatagtt accggataag gcgcagcggt cgggctgaac ggggggttcg | 6300 |
| tgcacacagc ccagcttgga gcgaacgacc tacaccgaac tgagatacct acagcgtgag | 6360 |
| ctatgagaaa gcgccacgct tcccgaaggg agaaaggcgg acaggtatcc ggtaagcggc | 6420 |
| agggtcggaa caggagagcg cacgagggag cttccagggg gaaacgcctg gtatctttat | 6480 |
| agtcctgtcg ggtttcgcca cctctgactt gagcgtcgat ttttgtgatg ctcgtcaggg | 6540 |
| gggcggagcc tatggaaaaa cgccagcaac gcggccttt tacggttcct ggccttttgc | 6600 |
| tggccttttg ctcacatgtt ctttcctgcg ttatccctg attctgtgga taaccgtatt | 6660 |
| accgcctttg agtgagctga taccgctcgc cgcagccgaa cgaccgagcg cagcgagtca | 6720 |
| gtgagcgagg aagcggaaga gcgcc | 6745 |

<210> SEQ ID NO 21
<211> LENGTH: 6718
<212> TYPE: DNA
<213> ORGANISM: Artificial
<220> FEATURE:
<223> OTHER INFORMATION: pks1-suc 2/lack

<400> SEQUENCE: 21

| | | |
|---|---|---|
| caatacgcaa accgcctctc cccgcgcgtt ggccgattca ttaatgcagc tggcacgaca | 60 |
| ggagctcaaa acgtaggggc aaacaaacgg aaaaatcgtt tctcaaattt tctgatgcca | 120 |
| agaactctaa ccagtcttat ctaaaaattg ccttatgatc cgtctctccg gttacagcct | 180 |
| gtgtaactga ttaatcctgc ctttctaatc accattctaa tgttttaatt aagggatttt | 240 |
| gtcttcatta acggctttcg ctcataaaaa tgttatgacg ttttgcccgc aggcgggaaa | 300 |
| ccatccactt cacgagactg atctcctctg ccggaacacc gggcatctcc aacttataag | 360 |
| ttggagaaat aagagaattt cagattgaga gaatgaaaaa aaaaaaaaaa aaaggcagag | 420 |
| gagagcatag aaatggggtt cacttttttgg taaagctata gcatgcctat cacatataaa | 480 |
| tagagtgcca gtagcgactt ttttcacact cgaaatactc ttactactgc tctcttgttg | 540 |
| tttttatcac ttcttgtttc ttcttggtaa atagaatatc aagctacaaa aagcatacaa | 600 |
| tcaactatca actattaact atatcgtaat actagtaaaa atgatgcttt tgcaagcttt | 660 |
| ccttttcctt ttggctggtt ttgcagccaa aatatctgca tctatgggat ccccggct | 720 |
| gcaggaattc gatatcaagc ttatcgatac cgtcgacctc gagtcatgta attagttatg | 780 |
| tcacgcttac attcacgccc tccccccaca tccgctctaa ccgaaaagga aggagttaga | 840 |
| caacctgaag tctaggtccc tatttatttt tttatagtta tgttagtatt aagaacgtta | 900 |

| | |
|---|---|
| tttatatttc aaattttct tttttttctg tacagacgcg tgtacgcatg taacattata | 960 |
| ctgaaaacct tgcttgagaa ggttttggga cgctcgaagg ctttaatttg cggccggtac | 1020 |
| ccaattcgcc ctatagtgag tcgtattacg cgcgctcact ggccgtcgtt ttacaacgtc | 1080 |
| gtgactggga aaaccctggc gttacccaac ttaatcgcct tgcagcacat cccccttcg | 1140 |
| ccagctggcg taatagcgaa gaggcccgca ccgatcgccc ttcccaacag ttgcgcagcc | 1200 |
| tgaatggcga atggacgcgc cctgtagcgg cgcattaagc gcggcgggtg tggtggttac | 1260 |
| gcgcagcgtg accgctacac ttgccagcgc cctagcgccc gctcctttcg ctttcttccc | 1320 |
| ttcctttctc gccacgttcg ccggctttcc ccgtcaagct ctaaatcggg ggctcccttt | 1380 |
| agggttccga tttagtgctt tacggcacct cgaccccaaa aaacttgatt agggtgatgg | 1440 |
| ttcacgtagt gggccatcgc cctgatagac ggtttttcgc cctttgacgt tggagtccac | 1500 |
| gttctttaat agtggactct tgttccaaac tggaacaaca ctcaaccccta tctcggtcta | 1560 |
| ttcttttgat ttataaggga ttttgccgat ttcggcctat tggttaaaaa atgagctgat | 1620 |
| ttaacaaaaa tttaacgcga attttaacaa aatattaacg tttacaattt cctgatgcgg | 1680 |
| tattttctcc ttacgcatct gtgcggtatt tcacaccgca tagggtaata actgatataa | 1740 |
| ttaaattgaa gctctaattt gtgagtttag tatacatgca tttacttata atacagtttc | 1800 |
| tggatggcgg cgttagtatc gaatcgacag cagtatagcg accagcattc acatacgatt | 1860 |
| gacgcatgat attactttct gcgcacttaa cttcgcatct gggcagatga tgtcgaggcg | 1920 |
| aaaaaaaata taaatcacgc taacatttga ttaaaataga acaactacaa tataaaaaaa | 1980 |
| ctatacaaat gacaagttct tgaaaacaag aatctttta ttgtcagtac tgattagaaa | 2040 |
| aactcatcga gcatcaaatg aaactgcaat ttattcatat caggattatc aataccatat | 2100 |
| ttttgaaaaa gccgtttctg taatgaagga gaaaactcac cgaggcagtt ccataggatg | 2160 |
| gcaagatcct ggtatcggtc tgcgattccg actcgtccaa catcaataca acctattaat | 2220 |
| ttccctcgt caaaaataag gttatcaagt gagaaatcac catgagtgac gactgaatcc | 2280 |
| ggtgagaatg gcaaaagctt atgcatttct ttccagactt gttcaacagg ccagccatta | 2340 |
| cgctcgtcat caaaatcact cgcatcaacc aaaccgttat tcattcgtga ttgcgcctga | 2400 |
| gcgagacgaa atacgcgatc gctgttaaaa ggacaattac aaacaggaat cgaatgcaac | 2460 |
| cggcgcagga acactgccag cgcatcaaca atattttcac ctgaatcagg atattcttct | 2520 |
| aatacctgga atgctgtttt gccggggatc gcagtggtga gtaaccatgc atcatcagga | 2580 |
| gtacggataa aatgcttgat ggtcggaaga ggcataaatt ccgtcagcca gtttagtctg | 2640 |
| accatctcat ctgtaacatc attggcaacg ctacctttgc catgtttcag aaacaactct | 2700 |
| ggcgcatcgg gcttcccata caatcgatag attgtcgcac ctgattgccc gacattatcg | 2760 |
| cgagcccatt tatacccata taaatcagca tccatgttgg aatttaatcg cggcctcgaa | 2820 |
| acgtgagtct tttccttacc catggttgtt tatgttcgga tgtgatgtga aactgtatc | 2880 |
| ctagcaagat tttaaaagga agtatatgaa agaagaacct cagtggcaaa tcctaacctt | 2940 |
| ttatatttct ctacaggggc gcggcgtggg acaattcaa cgcgtctgtg aggggagcgt | 3000 |
| ttccctgctc gcaggtctgc agcgaggagc cgtaattttt gcttcgcgcc gtgcggccat | 3060 |
| caaaatgtat ggatgcaaat gattatacat ggggatgtat gggctaaatg tacgggcgac | 3120 |
| agtcacatca tgccctgag ctgcgcacgt caagactgtc aaggagggta ttctgggcct | 3180 |
| tggtatggtg cactctcagt acaatctgct ctgatgccgc atagttaagc cagccccgac | 3240 |
| acccgccaac acccgctgac gcgccctgac gggcttgtct gctcccggca tccgcttaca | 3300 |

```
gacaagctgt gaccgtctcc gggagctgca tgtgtcagag gttttcaccg tcatcaccga   3360
aacgcgcgag acgaaagggc ctcgtgatac gcctattttt ataggttaat gtcatgataa   3420
taatggtttc ttagtatgat ccaatatcaa aggaaatgat agcattgaag gatgagacta   3480
atccaattga ggagtggcag catatagaac agctaagggg tagtgctgaa ggaagcatac   3540
gataccccgc atggaatggg ataatatcac aggaggtact agactacctt tcatcctaca   3600
taaatagacg catataagta cgcatttaag cataaacacg cactatgccg ttcttctcat   3660
gtatatatat atacaggcaa cacgcagata taggtgcgac gtgaacagtg agctgtatgt   3720
gcgcagctcg cgttgcattt tcggaagcgc tcgttttcgg aaacgctttg aagttcctat   3780
tccgaagttc ctattctcta gaaagtatag gaacttcaga gcgcttttga aaaccaaaag   3840
cgctctgaag acgcactttc aaaaaaccaa aaacgcaccg gactgtaacg agctactaaa   3900
atattgcgaa taccgcttcc acaaacattg ctcaaaagta tctctttgct atatatctct   3960
gtgctatatc cctatataac ctacccatcc acctttcgct ccttgaactt gcatctaaac   4020
tcgacctcta cattttttat gtttatctct agtattactc tttagacaaa aaaattgtag   4080
taagaactat tcatagagtg aatcgaaaac aatacgaaaa tgtaaacatt tcctatacgt   4140
agtatataga gacaaaatag aagaaaccgt tcataatttt ctgaccaatg aagaatcatc   4200
aacgctatca ctttctgttc acaaagtatg cgcaatccac atcggtatag aatataatcg   4260
gggatgcctt tatcttgaaa aaatgcaccc gcagcttcgc tagtaatcag taaacgcggg   4320
aagtggagtc aggctttttt tatggaagag aaaatagaca ccaaagtagc cttcttctaa   4380
ccttaacgga cctacagtgc aaaaagttat caagagactg cattatagag cgcacaaagg   4440
agaaaaaaag taatctaaga tgctttgtta gaaaaatagc gctctcggga tgcattttg   4500 tagaacaaaa aagaagtata gattctttgt tggtaaaata gcgctctcgc gttgcatttc   4560
tgttctgtaa aaatgcagct cagattcttt gtttgaaaaa ttagcgctct cgcgttgcat   4620
ttttgtttta caaaaatgaa gcacagattc ttcgttggta aaatagcgct ttcgcgttgc   4680
atttctgttc tgtaaaaatg cagctcagat tctttgtttg aaaaattagc gctctcgcgt   4740 tgcattttg ttctacaaaa tgaagcacag atgcttcgtt caggtggcac ttttcgggga   4800
aatgtgcgcg gaacccctat ttgtttattt ttctaaatac attcaaatat gtatccgctc   4860
atgagacaat aaccctgata aatgcttcaa taatattgaa aaaggaagag tatgagtatt   4920
caacatttcc gtgtcgccct tattcccttt tttgcggcat tttgccttcc tgttttgct   4980 cacccagaaa cgctggtgaa agtaaaagat gctgaagatc agttgggtgc acgagtgggt   5040
tacatcgaac tggatctcaa cagcggtaag atccttgaga gttttcgccc cgaagaacgt   5100
tttccaatga tgagcacttt taaagttctg ctatgtggcg cggtattatc ccgtattgac   5160
gccgggcaag agcaactcgg tcgccgcata cactattctc agaatgactt ggttgagtac   5220
tcaccagtca cagaaaagca tcttacggat ggcatgacag taagagaatt atgcagtgct   5280
gccataacca tgagtgataa cactgcggcc aacttacttc tgacaacgat cggaggaccg   5340
aaggagctaa ccgcttttt gcacaacatg gggatcatg taactcgcct tgatcgttgg   5400
gaaccggagc tgaatgaagc cataccaaac gacgagcgtg acaccacgat gcctgtagca   5460
atggcaacaa cgttgcgcaa actattaact ggcgaactac ttactctagc ttcccggcaa   5520
caattaatag actggatgga ggcggataaa gttgcaggac cacttctgcg ctcggccctt   5580
ccggctggct ggtttattgc tgataaatct ggagccggtg agcgtgggtc tcgcggtatc   5640
attgcagcac tggggccaga tggtaagccc tcccgtatcg tagttatcta cacgacgggg   5700
```

```
agtcaggcaa ctatggatga acgaaataga cagatcgctg agataggtgc ctcactgatt    5760
aagcattggt aactgtcaga ccaagtttac tcatatatac tttagattga tttaaaactt    5820 cattttttaat ttaaaaggat ctaggtgaag atccttttttg ataatctcat gaccaaaatc   5880
ccttaacgtg agttttcgtt ccactgagcg tcagaccccg tagaaaagat caaaggatct    5940
tcttgagatc ctttttttct gcgcgtaatc tgctgcttgc aaacaaaaaa accaccgcta    6000
ccagcggtgg tttgtttgcc ggatcaagag ctaccaactc ttttccgaa ggtaactggc    6060 ttcagcagag cgcagatacc aaatactgtc cttctagtgt agccgtagtt aggccaccac    6120
ttcaagaact ctgtagcacc gcctacatac ctcgctctgc taatcctgtt accagtggct    6180
gctgccagtg gcgataagtc gtgtcttacc gggttggact caagacgata gttaccggat    6240
aaggcgcagc ggtcgggctg aacggggggt cgtgcacac agcccagctt ggagcgaacg    6300
acctacaccg aactgagata cctacagcgt gagctatgag aaagcgccac gcttcccgaa    6360
gggagaaagg cggacaggta tccggtaagc ggcagggtcg gaacaggaga gcgcacgagg    6420
gagcttccag ggggaaacgc ctggtatctt tatagtcctg tcgggtttcg ccacctctga    6480
cttgagcgtc gatttttgtg atgctcgtca ggggggcgga gcctatggaa aaacgccagc    6540
aacgcggcct ttttacggtt cctggccttt tgctggcctt ttgctcacat gttctttcct    6600
gcgttatccc ctgattctgt ggataaccgt attaccgcct tgagtgagc tgataccgct    6660 cgccgcagcc gaacgaccga gcgcagcgag tcagtgagcg aggaagcgga agagcgcc     6718

<210> SEQ ID NO 22
<211> LENGTH: 2202
<212> TYPE: DNA
<213> ORGANISM: Artificial
<220> FEATURE:
<223> OTHER INFORMATION: 33851 PMA1

<400> SEQUENCE: 22
gagctcgaat tctgtgggtg accagccggc agctgcagca agaataagat aaaacaacta      60
tggagactga tgtaaaatata cttgaagccg ggcaataata taagcaccgt gagccgattc     120
tcctcgatcc tacactgcac catataacga atggtcttgg actatggaag gcagtaacca     180
acaacagaaa agagagatta attagaaaaa gacatttgtc gagagaaaaa agtaaagac      240 cttatcgtac aactgttact gacatttttta ttttaagaag ctaaacccttt attattagcg    300 cgcccaagta ggcgcaaaac tagagaagtc gcagatgcat ccacccactt tttgccttat     360
ttttccttaa tttcagaaat atagttaaaa tgaaaaacaa ggacaagaaa agaacgggaa     420
aaagaaaagg gggattagca acaaagaaa agtccaataa atgattaca gacagcattg      480 gatgcgatga gatggcaacc agcgagatga gagcatagga ttttcatcct agctgcttta     540
gggaagacgc acaaaacttt gttatgtttg tagtaaatat agaaaagaaa acaaaaaagt     600
gctcggacga atccggtaga gctgtgtcta gcctcaataa gtttgccgca tttggtaaat     660
caaaactgtt tttctctccg tcatttgttt tgaagcttgt tctgttagtt tagggaaata     720
gaaaaaaaaa aaagggaaa aagaaagaaa tcatatgccc aatggagtac gagaattggg     780
gaaaaagcct ccatcgggtt tttaaacggg cgtatacatg cttaccacac tcccgtaagc    840
aagaacaaag aatttatctt gataaactgc gtaataagtc aatcaattgc tctatatacg    900
cgcatatacg taaaacacag aatcacattt tagtcaggcc caagccgtat agggcgaaaa    960
agcccgcgct tatcaagtca tcgtaacgaa tcagatcttt ccaactgcta tcgcatacgt   1020
aagagaattg aaatatttct cgggtacgat acgacatttt ttctttacat ttctttacta   1080
```

```
aacccgacgg cacgggaaag aagatgagac tcggaacgga agctagaaga aaaaggaagg   1140
acacagagat tttccgagat taactcagct ttgctaaagt gcaaaaagtc gtttacgtca   1200
ccatcgctga cggggaaaaa acaaaacaag tctagatgtg ggtgaccagc cggcaggaat   1260
tccttcctga aacggagaaa cataaacagg cattgctggg atcacccata catcactctg   1320
ttttgcctga ccttttccgg taatttgaaa acaaacccgg tctcgaagcg gagatccggc   1380
gataattacc gcagaaataa acccatacac gagacgtaga accagccgca catggccgga   1440
gaaactcctg cgagaatttc gtaaactcgc gcgcattgca tctgtatttc ctaatgcggc   1500
acttccaggc gtcgagacct ctgacatgct tttgacagga atagacattt tcagaatgtt   1560
atccatatgc ctttcggggtt ttttttcctttc cttttccatc atgaaaaatc tctcgacacc   1620
gtttatccat tgcttttttg ttgtcttttt ccctcgttca cagaaagtct gaagaagcta   1680
tagtagaact atgagctttt tttgtttctg ttttcctttt tttttttttt acctctgtgg   1740
aaattgttac tctcacactc tttagttcgt ttgtttgttt tgtttattcc aattatgacc   1800
ggtgacgaaa cgtggtcgat ggtgggtacc gcttatgctc ccctccatta gtttcgatta   1860
tataaaaagg ccaaatattg tattattttc aaatgtccta tcattatcgt ctaacatcta   1920
atttctctta aattttttct ctttctttcc tataacacca atagtgaaaa tcttttttc    1980 ttctatatct acaaaaactt ttttttttcta tcaacctcgt tgataaattt tttcttttaac  2040 aatcgttaat aattaattaa ttggaaaata accatttttt ctctcttta tacacacatt    2100 caaaagaaag aaaaaaaata taccccagct agttaaagaa aatcattgaa aagaataaga   2160
agataagaaa gatttaatta tcaaacaata tcaataacta gt                     2202

<210> SEQ ID NO 23
<211> LENGTH: 776
<212> TYPE: DNA
<213> ORGANISM: Artificial
<220> FEATURE:
<223> OTHER INFORMATION: 33852 TDH2

<400> SEQUENCE: 23
gagctcgaat tctgtgggtg accagccggc agctgcagaa taaaaaacac gcttttttcag    60 ttcgagttta tcattatcaa tactgccatt tcaaagaata cgtaaataat taatagtagt   120
gattttccta actttatttta gtcaaaaaat tagccttta attctgctgt aacccgtaca   180
tgcccaaaat aggggcggg ttacacagaa tatataacat cgtaggtgtc tgggtgaaca    240
gtttattcct ggcatccact aaatataatg gagcccgctt tttaagctgg catccagaaa   300 aaaaagaat cccagcacca aaatattgtt tccttcacca accatcagtt cataggtcca    360
ttctcttagc gcaactacag agaacagggg cacaaacagg caaaaaacgg cacaacctc    420 aatggagtga tgcaacctgg tctagatgtg ggtgaccagc cggcaggaat tcctggagta   480
aatgatgaca caaggcaatt gacccacgca tgtatctatc tcatttttctt acaccttcta   540 ttaccttctg ctctctctga tttggaaaaa gctgaaaaaa aaggttgaaa ccagttccct   600
gaaattattc ccctacttga ctaataagta tataaagacg gtaggtattg attgtaattc   660
tgtaaatcta tttcttaaac ttcttaaatt ctacttttat agttagtctt ttttttagtt   720
ttaaaacacc aagaacttag tttcgaataa acacacataa acaaacaaaa actagt       776

<210> SEQ ID NO 24
<211> LENGTH: 1134
<212> TYPE: DNA
<213> ORGANISM: Artificial
```

```
<220> FEATURE:
<223> OTHER INFORMATION: 33853 ILV5

<400> SEQUENCE: 24
gagctcgaat tctgtgggtg accagccggc agctgcagat gttttttactt ctgtatatcg      60 tgaagtagta agtgataagc gaatttggct aagaacgttg taagtgaaca agggacctct     120
tttgcctttc aaaaaaggat taaatggagt taatcattga gatttagttt tcgttagatt     180
ctgtatccct aaataactcc cttacccgac gggaaggcac aaaagacttg aataatagca     240
aacggccagt agccaagacc aaataatact agagttaact gatggtctta aacaggcatt     300
acgtggtgaa ctccaagacc aatatacaaa atatcgataa gttattcttg cccaccaatt     360
taaggagcct acatcaggac agtagtacca ttcctcagag aagaggtata cataacaaga     420
aaatcgcgtg aacaccttat ataacttagc ccgttattga gctaaaaaac cttgcaaaat     480
ttcctatgaa taagaatact tcagacgtga taaaaattta ctttctaact cttctcacgc     540
tgcccctatc tgttcttccg ctctaccgtg agaaataaag catcgagtac ggcagttcgc     600
tgtcactgaa ctaaaacaat aaggctagtt ctagatgtgg gtgaccagcc ggcaggaatt     660
cgaatgatga acttgcttgc tgtcaaactt ctgagttgcc gctgatgtga cactgtgaca     720
ataaattcaa accggttata gcggtctcct ccggtaccgg ttctgccacc tccaatagac     780
ctcagtagga gtcagaacct ctgcggtggc tgtcagtgac tcatccgcgt ttcgtaagtt     840
gtgcgcgtgc acatttcgcc cgttcccgct catcttgcag caggcgaaat tttcatcacg     900
ctgtaggacg caaaaaaaaa ataattaatc gtacaagaat cttggaaaaa aaattgaaaa     960
attttgtata aagggatga cctaacttga ctcaatggct tttacaccca gtattttccc     1020
tttccttgtt tgttacaatt atagaagcaa gacaaaaaca tatagacaac ctattcctag    1080
gagttatatt tttttaccct accagcaata taagtaaaaa ataaaacaac tagt           1134

<210> SEQ ID NO 25
<211> LENGTH: 711
<212> TYPE: DNA
<213> ORGANISM: Artificial
<220> FEATURE:
<223> OTHER INFORMATION: 33854 FBA1

<400> SEQUENCE: 25
gagctcgaat tctgtgggtg accagccggc agctgcagaa taacaatact gacagtacta      60
aataattgcc tacttggctt cacatacgtt gcatacgtcg atatagataa taatgataat     120
gacagcagga ttatcgtaat acgtaatagt tgaaaatctc aaaaatgtgt gggtcattac     180
gtaaataatg ataggaatgg gattcttcta ttttttcctt ttccattcta gcagccgtcg     240
ggaaaacgtg gcatcctctc tttcgggctc aattggagtc acgctgccgt gagcatcctc     300
tctttccata tctaacaact gagcacgtaa ccaatggaaa agcatgagct tagcgttgct     360
ccaaaaaagt attggatggt taatctagat gtgggtgacc agccggcagg aattctacca     420
tttgtctgtt ctcttctgac tttgactcct caaaaaaaaa aaatctacaa tcaacagatc     480
gcttcaatta cgccctcaca aaaacttttt tccttcttct tcgcccacgt taaattttat     540
ccctcatgtt gtctaacgga tttctgcact tgatttatta taaaaagaca aagacataat     600
acttctctat caatttcagt tattgttctt ccttgcgtta ttcttctgtt cttcttttc      660 ttttgtcata tataaccata accaagtaat acatattcaa aatggactag t              711

<210> SEQ ID NO 26
<211> LENGTH: 674
```

<212> TYPE: DNA
<213> ORGANISM: Artificial
<220> FEATURE:
<223> OTHER INFORMATION: 33855 DLD1

<400> SEQUENCE: 26

```
gagctcgaat tctgtgggtg accagccggc agctgcagac ttggtcttac gctactgctg      60
ctgctaacgc tgctgctgct tttgctcata tgcttccatt gaccgtcatt agtatcagcg     120
tcagcctttt tgacataagc caccgctctg tcagggtaac cctatgaaac atttcaaaac     180
gttataaagg aactcgtctg gttacaacaa ggaaatatca ctacaaacag ctgtccgtac     240
ggctcctcaa ctctctcaat gttgttcgcc tggtcacaca cagcatagtt tcgtcattcg     300
gcgccgacgg tcgctgtctc ttggagcctt caagctcttg tcaacccagg tccgttgtgc     360
ctctagatgt gggtgaccag ccggcaggaa ttcgataaaa gtaacagcag accccacgc      420
ccgcatccca ctctcttctc cgaccacctc cctcgaagtt cttccctgcc aatcccacgt     480
cgatccagcg tagttggccc caactggtgc agtaataacc gcttagcgat tttgcactcg     540
gaactacata tgtatatata tatgtgtgtg tgtgtgtggg ctggaaagat ttcttgagct     600
tccgtgttat agtgcaattt aaatattgta catcattccg atccagctgg aaacaaaagc     660
aagaacaaac tagt                                                       674
```

<210> SEQ ID NO 27
<211> LENGTH: 1482
<212> TYPE: DNA
<213> ORGANISM: Artificial
<220> FEATURE:
<223> OTHER INFORMATION: 33856 CWP2

<400> SEQUENCE: 27

```
gagctcgaat tctgtgggtg accagccggc agctgcagat tatgtatttc gagcatgcat      60
ctggaaccta tgtttacata cgtacaaacg gtatttaaaa gtttctattc ttagcgtcaa     120
ttgccccttta tcgttttgtt aaccaattgt tgttttttatt cattatgcca tgacccgaaa    180
aatgagcaaa atcggtcaaa gtaaatagct aaatatttgg tctaaaaagt aagagagaaa     240
tgaaaatggc aaggcttaac tactttgcaa tagtgtatat agacattacc aattgagtcc     300
agcaacgaaa gattccgctt gcacttggtc aatcatttac tgaccataat cgaagtaat      360
agagatgcta ctaaaagatg accatgcgat tacaatttac aatagacaat taagcgcaag     420
gacaatcagt atgcattcca tttctaatag acaaggtgct atgagtgaat tgctagcctc     480
cccttttat tttgtgcggt caccgcaagg acaaagctt ttcttagaaa accgtctgag      540
aagcataacg tacgccatcc cctagacata ttaataatgc tacagatact atgctgctcg     600
tctttttttg acgaccctct agatgtgggt gaccagccgg caggaattct tttattgcaa     660
tgtgcaacta atggcaaaca accacatagt atcacagtat tacattgcct ccaccgatgc     720
ggatgttagg gcgccaagtc tgtcatgaag catgttcctg tcataatctt gtatgcaaaa     780
taccgcgttc tgcgccactg atatgctagg cagcagcaac ctatgcagaa gattgctttt     840
cccacgcctg ttttacgtct ccagggcact tgaaacaatg cagcgatcgc cgccacaaca     900
cgccaaagag aagcgaaagt gggcctgggc ggcctcagtt tcggcagagg taaacaacac     960
gaactgaact gccttagctc cgaagggcaa ttccacaggc actccgcggg gcccggcaa     1020
ggcccaaaag gcgtggaata tgcgcgtttt ggggccataa cacccagtac cacggccgga    1080
acgggccata taataagttt ttcactctca agaatggtaa acgtaaatag gaacatccca    1140
ctaccctaga aattgcggaa atttcgcgct tatcattaga aaatctggaa ccgtcctttt    1200
```

```
tcctctttct tgcatttccc tttccgtatt attgccattc tttaactgca tttggggaac    1260
cgtagaccaa aagccaaaca gagaaatgta acgttctaaa aaaaaaacaa cgaaaaaatt    1320
gaaaaataag atacaataat cgtatataaa tcaggcttct tgttcatcat tttcaattct    1380
cttcttgcca tcccttttcc tatctttgtt cttttcttct cataatcaag aataaataac    1440
ttcatcacat tcgctacaca ctaacaagaa aaaaaaacta gt                       1482
```